United States Patent
Boyer et al.

(10) Patent No.: US 12,274,409 B2
(45) Date of Patent: Apr. 15, 2025

(54) THROUGH OPENING AIR KNIFE FOR HIGH SPEED REUSABLE BEVERAGE CONTAINER WASHING SYSTEM

(71) Applicant: Midea Group Co., Ltd., Foshan (CN)

(72) Inventors: Joel Boyer, Louisville, KY (US); Robert M. Digman, Goshen, KY (US)

(73) Assignee: MIDEA GROUP CO., LTD., Guangdong (CN)

( * ) Notice: Subject to any disclaimer, the term of this patent is extended or adjusted under 35 U.S.C. 154(b) by 363 days.

(21) Appl. No.: 17/934,061

(22) Filed: Sep. 21, 2022

(65) Prior Publication Data
US 2023/0095081 A1 Mar. 30, 2023

Related U.S. Application Data

(63) Continuation-in-part of application No. 17/490,888, filed on Sep. 30, 2021, now Pat. No. 12,201,257, and a continuation-in-part of application No. 17/490,884, filed on Sep. 30, 2021, now Pat. No. 12,035,865.

(51) Int. Cl.
| | |
|---|---|
| *A47L 15/48* | (2006.01) |
| *A47L 15/00* | (2006.01) |
| *A47L 15/42* | (2006.01) |
| *A61L 2/10* | (2006.01) |

(52) U.S. Cl.
CPC ......... *A47L 15/486* (2013.01); *A47L 15/0065* (2013.01); *A47L 15/0076* (2013.01); *A47L 15/4242* (2013.01); *A47L 15/4257* (2013.01); *A61L 2/10* (2013.01); *A61L 2202/17* (2013.01); *A61L 2202/23* (2013.01)

(58) Field of Classification Search
CPC ............... A47L 15/486; A47L 15/0065; A47L 15/0076; A47L 15/4242; A47L 15/4257; A61L 2/10; A61L 2202/17; A61L 2202/23
USPC ....................................................... 134/58 D
See application file for complete search history.

(56) References Cited

U.S. PATENT DOCUMENTS

| | | | |
|---|---|---|---|
| 1,502,131 | A | 2/1922 | Vaudreuil |
| 1,680,962 | A | 8/1928 | Voshardt |
| 1,859,302 | A | 5/1932 | Lederman |
| 1,876,895 | A | 9/1932 | James |
| 2,263,807 | A | 11/1941 | Hanson |
| 2,634,736 | A | 4/1953 | Bewen |
| 2,764,017 | A | 9/1956 | Ronnebeck |
| 2,943,474 | A | 7/1960 | Bochan |
| 2,970,700 | A | 2/1961 | Lacy et al. |

(Continued)

FOREIGN PATENT DOCUMENTS

| | | |
|---|---|---|
| CN | 2834716 Y | 11/2006 |
| CN | 201529653 U | 7/2010 |

(Continued)

OTHER PUBLICATIONS

Graf, Irina, United States Patent and Trademark Office, Notice of Allowance issued in U.S. Appl. No. 17/490,884, 25 pages, dated Mar. 4, 2024.

(Continued)

*Primary Examiner* — Tinsae B Ayalew
(74) *Attorney, Agent, or Firm* — Gray Ice Higdon

(57) ABSTRACT

A beverage container washing system may utilize a through opening air knife to direct a flow of pressurized fluid through an opening in a concentric housing member of a beverage container washing system and onto a beverage container disposed within a wash chamber thereof.

19 Claims, 13 Drawing Sheets

(56) References Cited

U.S. PATENT DOCUMENTS

| | | | |
|---|---|---|---|
| 3,060,946 A | 10/1962 | David |
| 3,122,148 A | 2/1964 | Alabaster |
| 3,204,273 A | 9/1965 | Gallo |
| 3,312,230 A | 4/1967 | Thring |
| 3,370,597 A | 2/1968 | Fox |
| 4,326,551 A | 4/1982 | Voorhees |
| 4,444,213 A | 4/1984 | Taylor |
| 4,561,904 A | 12/1985 | Eberhardt, Jr. |
| 4,580,421 A | 4/1986 | Babuin et al. |
| 4,634,052 A | 1/1987 | Grizzle et al. |
| 4,681,260 A | 7/1987 | Cochran |
| 4,689,089 A | 8/1987 | Eberhardt, Jr. et al. |
| 5,315,729 A | 5/1994 | Yang |
| 5,343,886 A | 9/1994 | Beswick |
| 5,531,383 A | 7/1996 | Pacht et al. |
| 5,640,981 A | 6/1997 | Niemela et al. |
| 5,675,880 A | 10/1997 | Saikin |
| 5,704,380 A | 1/1998 | Zelniker et al. |
| 5,903,944 A | 5/1999 | Burrell |
| 5,904,163 A | 5/1999 | Inoue et al. |
| 6,086,222 A | 7/2000 | Juba et al. |
| 6,110,424 A | 8/2000 | Maiden et al. |
| 6,517,776 B1 | 2/2003 | Rodgers et al. |
| 6,550,489 B1 | 4/2003 | Yates |
| 6,579,495 B1 | 6/2003 | Maiden |
| 6,691,536 B2 | 2/2004 | Severns et al. |
| 6,732,950 B2 | 5/2004 | Ingham, Jr. et al. |
| 6,799,732 B2 | 10/2004 | Sirkin |
| 6,926,017 B2 | 8/2005 | Halbmaier |
| 7,236,099 B2 | 6/2007 | Schult |
| 7,550,935 B2 | 6/2009 | Lys et al. |
| 7,674,001 B1 | 3/2010 | Ferrin et al. |
| 7,882,591 B2 | 2/2011 | Arnold |
| 8,136,742 B2 | 3/2012 | Cordua |
| 8,146,612 B2 | 4/2012 | Brunswick et al. |
| 8,297,533 B2 | 10/2012 | Dunn et al. |
| 8,303,728 B2 | 11/2012 | Peukert et al. |
| 8,500,919 B1 | 8/2013 | Al-qaffas |
| 8,810,423 B2 | 8/2014 | Kaczmarek et al. |
| 8,905,014 B2 | 12/2014 | Shaffer |
| 9,138,768 B2 | 9/2015 | Jahan et al. |
| 9,146,032 B2 | 9/2015 | Maxwell |
| 9,378,988 B2 | 6/2016 | Osada et al. |
| 9,474,432 B2 | 10/2016 | Alexander |
| 9,566,617 B2 | 2/2017 | Jensen et al. |
| 9,596,972 B2 | 3/2017 | Sonoda |
| 9,623,447 B2 | 4/2017 | Kataoka |
| 9,707,306 B2 | 7/2017 | Farren |
| 9,955,844 B2 | 5/2018 | Fletty et al. |
| 10,047,922 B2 | 9/2018 | Chien |
| 10,415,176 B2 | 9/2019 | Abramovich et al. |
| 10,670,619 B2 | 6/2020 | Schulze et al. |
| 10,893,790 B2 | 1/2021 | Ashworth et al. |
| 10,921,059 B2 | 2/2021 | Newland, III et al. |
| 11,166,617 B2 | 11/2021 | Yoon et al. |
| 11,241,137 B1 | 2/2022 | Ferguson et al. |
| 11,253,131 B2 | 2/2022 | Kwon |
| 2003/0150475 A1 | 8/2003 | Abrams et al. |
| 2005/0072449 A1 | 4/2005 | Alpert |
| 2005/0230638 A1 | 10/2005 | Ancona et al. |
| 2006/0011263 A1 | 1/2006 | Till |
| 2007/0246071 A1 | 10/2007 | Streb |
| 2010/0132111 A1 | 6/2010 | Na |
| 2011/0203616 A1 | 8/2011 | Berner et al. |
| 2012/0141322 A1 | 6/2012 | Fogg |
| 2013/0198786 A1 | 8/2013 | Cook et al. |
| 2016/0367931 A1 | 12/2016 | Yin |
| 2018/0028044 A1 | 2/2018 | Anim-Mensah et al. |
| 2018/0092505 A1 | 4/2018 | Simon |
| 2018/0236398 A1 | 8/2018 | Heer et al. |
| 2018/0318886 A1 | 11/2018 | Libbrecht et al. |
| 2018/0338665 A1 | 11/2018 | Foehringer |
| 2018/0354467 A1 | 12/2018 | Glickman et al. |
| 2019/0358682 A1 | 11/2019 | Borghi et al. |
| 2020/0216332 A1 | 7/2020 | Li |
| 2020/0253450 A1 | 8/2020 | Kafzan et al. |
| 2020/0289685 A1 | 9/2020 | Li |
| 2020/0337522 A1 | 10/2020 | Brewer et al. |
| 2021/0113054 A1 | 4/2021 | Son et al. |
| 2021/0161356 A1 | 6/2021 | Luu et al. |
| 2021/0178434 A1 | 6/2021 | Van Pottelbergh et al. |
| 2022/0018531 A1 | 1/2022 | Mo et al. |
| 2022/0079413 A1 | 3/2022 | Longo et al. |
| 2023/0097782 A1 | 3/2023 | Trice et al. |
| 2023/0100978 A1 | 3/2023 | Boyer et al. |
| 2023/0101333 A1 | 3/2023 | Boyer et al. |
| 2023/0101384 A1 | 3/2023 | Longo et al. |
| 2023/0101450 A1 | 3/2023 | Boyer et al. |
| 2023/0102987 A1 | 3/2023 | Boyer et al. |
| 2023/0112411 A1 | 4/2023 | Digman et al. |

FOREIGN PATENT DOCUMENTS

| | | |
|---|---|---|
| CN | 102324396 A | 1/2012 |
| CN | 203426095 U | 2/2014 |
| CN | 204363929 U | 6/2015 |
| CN | 205110293 U | 3/2016 |
| CN | 105534437 A | 5/2016 |
| CN | 109876169 A | 6/2019 |
| CN | 209915722 U | 1/2020 |
| CN | 209967112 U | 1/2020 |
| CN | 212166190 U | 12/2020 |
| CN | 213191400 U | 5/2021 |
| CN | 213551016 U | 6/2021 |
| CN | 113500070 A | 10/2021 |
| CN | 113953276 A | 1/2022 |
| CN | 113953280 A | 1/2022 |
| CN | 113953281 A | 1/2022 |
| DE | 4229250 A1 | 3/1994 |
| DE | 19618770 A1 | 11/1997 |
| DE | 102012109360 A1 | 5/2014 |
| DE | 102014222586 A1 | 5/2016 |
| DE | 102019214059 A1 | 3/2021 |
| EP | 1120121 A2 | 8/2001 |
| EP | 3636333 A1 | 4/2020 |
| EP | 3967207 A1 | 3/2022 |
| ES | 1265944 U | 4/2021 |
| FR | 1426408 A | 1/1966 |
| FR | 3068232 A1 | 1/2019 |
| IL | 108864 A | 3/1999 |
| JP | 2001247108 A | 9/2001 |
| KR | 20030017203 A | 3/2003 |
| KR | 101630417 B1 | 6/2016 |
| KR | 20160065051 A | 6/2016 |
| KR | 20180051462 A | 5/2018 |
| KR | 101885722 B1 | 9/2018 |
| KR | 101983721 B1 | 5/2019 |
| KR | 101987953 B1 | 6/2019 |
| KR | 102052837 B1 | 12/2019 |
| WO | WO0244637 A1 | 6/2002 |
| WO | WO2005087276 A2 | 9/2005 |
| WO | WO2007038904 A1 | 4/2007 |
| WO | WO2010132022 A2 | 11/2010 |
| WO | WO2020083851 A1 | 4/2020 |
| WO | WO2020212927 | 10/2020 |
| WO | 2020223540 A1 | 11/2020 |

OTHER PUBLICATIONS

Related Applications Transmittal.
YBB, YBB Professional Cup Washing Machine Tables Glass Rinser, Pitcher Rinser for Bar Café Household (Counter Top), retrieved from: https://www.amazon.com/YBB-Professional-Pitcher-Plating-Household/dp/B01MG7GPIR; Oct. 31, 2016.
Jectse, Cup Rinser, Automatic Household Commercial Cup Washer High-Pressure Cup Washer Cleaner Rinser Bar Accessories Home, Restaurant, Bar, Tea Shop, Coffee Shop, etc., Retrieved from: https://www.amazon.com/Automatic-Commercial-high-Pressure-Accessories-Restaurant/dp/B0868M9J9R, Mar. 23, 2020.
Hobart, Cleaning of Reusable Cups, Retrieved from: https://www.hobart-export.com/market-solutions/industry/cup-cleaning; Retrieved on: Sep. 23, 2021.

(56) References Cited

OTHER PUBLICATIONS

Webstaurantstore, Champion CG4 Low Temperature 48" Pass-Through Glass Washer, Left to Right—208/230V, Retrieved from: https://www.webstaurantstore.com/champion-cg4-low-temperature-48-pass-through-glass-washer-left-to-right-208-230v/253CG4LRV.html, Retrieved on: Sep. 23, 2021.

Northern Brewer, Vinator Bottle Rinser, Retrieved from: https://www.northernbrewer.com/products/vinator-bottle-rinser, Retrieved on Sep. 27, 2021.

Babymoov, Babymoov Turbo Pure Sterilizer & Dryer (2020), KiddiesKingdom.com, Retrieved from:https://www.kiddies-kingdom.com/health-hygiene/36070-babymoov-turbo-pure-sterilizer-dryer-2020.html, 2020.

Exair, High Efficiency Fixed Aluminum Air Amplifier, Inlet Dia.: 2.0 in, Grainger.com, Retrieved from: https://www.grainger.com/product/4LCX5?ef_id=EAIaIQobChMIotPGscCI8gIVZGxvBB3KTQnjEAQYAyABEgJDjfD_BwE:G:s&s_kwcid=AL!2966!3!281698275816!!!g!469974894180!&gucid=N:N:PS:Paid, Retrieved on: Sep. 27, 2021.

Solvair, Food & Beverage, Retrieved from: https://www.solvair.co.uk/applications/food-and-beverage/; Retrieved on: Sep. 27, 2021.

Costway, Full-Automatic Washing Machine 7.7 lbs Washer, Retrieved from: https://www.walmart.com/ip/Full-Automatic-Washing-Machine-7-7-lbs-Washer-Spinner-Germicidal-UV-Light-Blue/354269146, Retrieved on Sep. 27, 2021.

KaTom, Perlick PKBR24 24" Underbar Glass Washer, Retrieved from: https://www.katom.com/199-PKBR24.html?gclid=EAIaIQobChMI_aLznJmE8gIV2wytBh3yjwItEAQYBSABEgLu_vD_BwE, Retrieved on Sep. 27, 2021.

Gosain, Gaurav, A More Sustainable Dishwasher, ME589: Sustainable Design, Dec. 16, 2013.

Dongguan Vistech Import & Export Co., LTD, Mini UV Lamp Ultraviolet Germicidal Disinfection Lamp Portable UV Handheld Home Travel Ozone Sterilizer Light, Retrieved from: https://dgvistech.en.made-in-china.com/product/eZixUMaChJkH/China-Mini-UV-Lamp-Ultraviolet-Germicidal-Disinfection-Lamp-Portable-UV-Handheld-Home-Travel-Ozone-Sterilizer-Light.html, Retrieved on Sep. 30, 2021.

UVclean, UV-C Sanitizing Light Disinfection Telescoping Room Robot: Glow Trolley, Retrieved from: https://uvcleanhouse.com/products/glow-trolley, Retrieved on Sep. 30, 2021.

Meiko, Efficient Cleaning of Cups and Bottles, Retrieved from: https://www.meiko.info/en/efficient-cleaning-of-cups-and-bottles, Retrieved on Jan. 27, 2021.

Graf, Irina, United States Patent and Trademark Office, Non-Final Office Action issued in U.S. Appl. No. 17/490,884, 90 pages, dated Sep. 8, 2023.

Ayalew, Tinsae B., United States Patent and Trademark Office, Non-Final Office Action issued in U.S. Appl. No. 17/490,888, 28 pages, dated May 29, 2024.

Ayalew, Tinsae B., United States Patent and Trademark Office, Notice of Allowance issued in U.S. Appl. No. 17/490,888, 25 pages, dated Sep. 11, 2024.

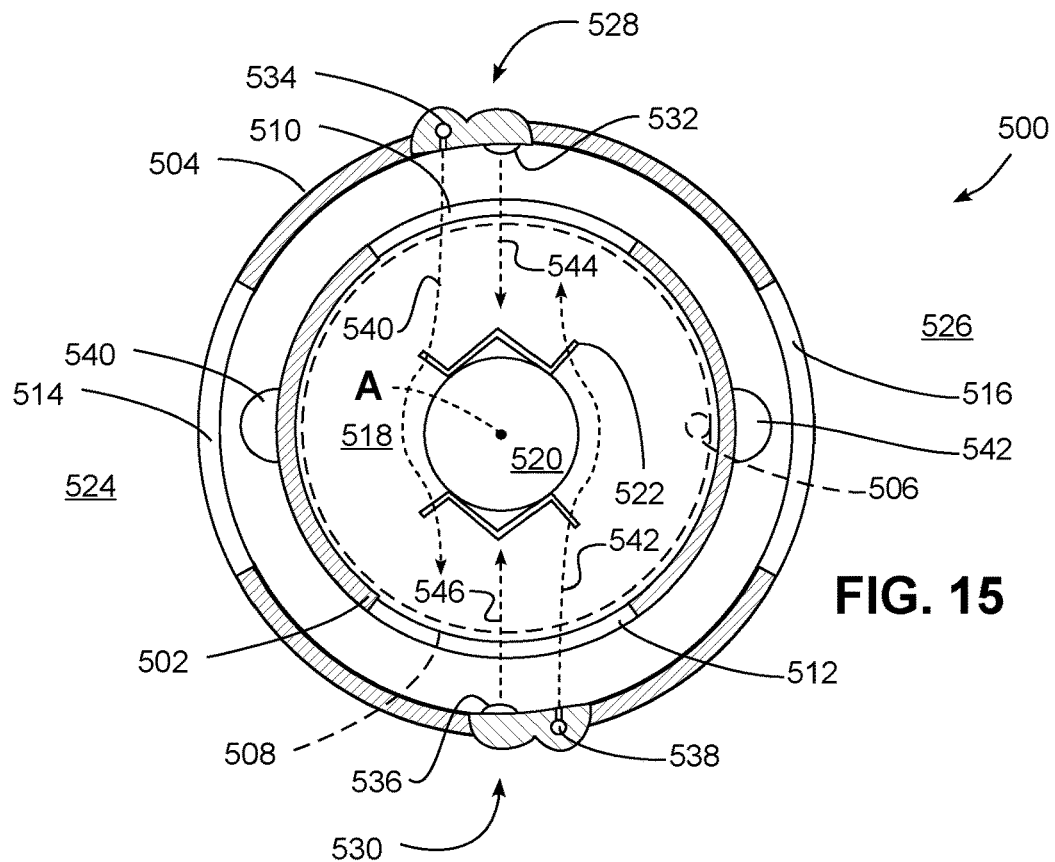
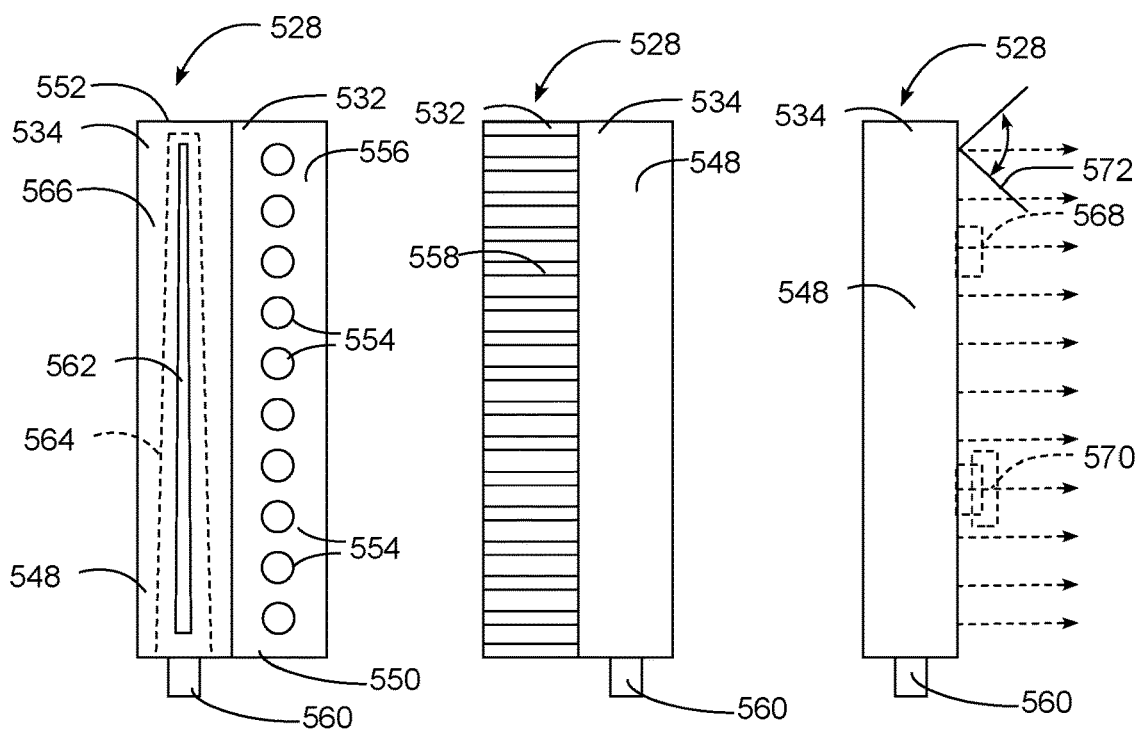
FIG. 15
FIG. 16    FIG. 17    FIG. 18

THROUGH OPENING AIR KNIFE FOR HIGH SPEED REUSABLE BEVERAGE CONTAINER WASHING SYSTEM

BACKGROUND

Due in part to the environmental concerns associated with disposable or single use beverage containers, many consumers are increasingly opting to use reusable cups, reusable bottles and other types of reusable beverage containers. In addition, some retail establishments, such as coffee shops, donut shops, and restaurants, have been willing to fill customer-provided cups and other beverage containers, and some have even introduced reusable cup programs where customers are able to purchase a reusable cup at a low initial cost when purchasing a beverage and then present that same cup at a later date for a refill.

While such programs have proven to be beneficial for both consumers and retail establishments, ensuring that the reusable cups are clean and sanitary prior to filling can be a challenge. Some municipalities, for example, have instituted ordinances that require a retail establishment to clean a work space after handling a customer-supplied reusable cup. Furthermore, pandemic-related concerns have led many retail establishments to discontinue the use of reusable cups due to the potential for a transmission of germs or contamination.

Retail establishments that serve beverages often use commercial-style dishwashers to wash cups and other utensils. Such dishwashers, however, are often configured to handle a large number of utensils in each load, and even the fastest dishwashers can still have runtimes of several minutes or more. Such dishwashers are also relatively large and noisy, and as a result are often placed in a kitchen or other area that is outside of the range of customers. As a result, traditional commercial-style dishwashers have a number of characteristics that make them generally unsuitable for use in connection with cleaning customer-provided reusable beverage containers.

Therefore, a significant need exists in the art for a system capable of washing reusable cups and other beverage containers in a fast and sanitary manner, and in particular, a system capable of being utilized in a retail establishment to clean customer-provided reusable beverage containers prior to filling, and to do so in a manner that is both fast and compatible with a fast-paced retail environment.

SUMMARY

The herein-described embodiments address these and other problems associated with the art by incorporating a through opening air knife in a beverage container washing system that may be used for rapid washing and/or sanitizing of beverage containers, e.g., for use in a retail environment to wash and/or sanitize customer-provided beverage containers prior to filling the beverage containers with purchased beverages, among other applications. The beverage container washing system may include concentric housing members, with an inner concentric housing member including an opening that, when rotated to a first position, provides external access to a wash chamber, and when rotated to a second position, is aligned with the through opening air knife such that the through opening air knife is able to direct a flow of pressurized fluid through the opening and onto a beverage container disposed within the wash chamber.

Therefore, consistent with one aspect of the invention, an apparatus for washing a beverage container may include first and second concentric housing members, each of the first and second concentric housing members including an opening, and one of the first and second concentric housing members being disposed inwardly from the other of the first and second concentric housing members and defining at least a portion of a wash chamber, where the first concentric housing member is rotatable about an axis of rotation between first and second positions, where when in the first position, the opening of the first concentric housing member is aligned with the opening of the second concentric housing member to provide external access to the wash chamber, and when in the second position, the opening of the first concentric housing member is unaligned with the opening of the second concentric housing member to restrict external access to the wash chamber, and an air knife positioned to direct air flow through the opening of the one of the first and second concentric housing members that is disposed inwardly from the other of the first and second concentric housing members and into the wash chamber when the first concentric housing member is disposed in the second position.

In some embodiments, the first concentric housing member is disposed inwardly from the second concentric housing member. Also, in some embodiments, the second concentric housing member is stationary. Further, in some embodiments, the air knife is mounted to the second concentric housing member. In some embodiments, the opening of the first concentric housing member is a first opening and the first concentric housing member includes a second opening, the opening of the second concentric housing member is a first opening and the second concentric housing member includes a second opening, and the second openings of the first and second concentric housing members are aligned with one another when the first concentric housing member is in the first position.

In addition, in some embodiments, the air knife is a first air knife, and the apparatus further includes a second air knife positioned to direct air flow through the second opening of the one of the first and second concentric housing members that is disposed inwardly from the other of the first and second concentric housing members and into the wash chamber when the first concentric housing member is disposed in the second position. In some embodiments, the first and second openings of the first concentric housing member are about 180 degrees offset from one another about the axis of rotation, the first and second openings of the second concentric housing member are about 180 degrees offset from one another about the axis of rotation, and the first and second air knife are about 180 degrees offset from one another about the axis of rotation. In addition, in some embodiments, the first air knife is oriented to direct air flow along a first side of the beverage container and the second air knife is oriented to direct air flow along a second side of the beverage container that is opposite the first side of the beverage container.

Moreover, in some embodiments, the air knife includes a housing and an air channel disposed within the housing. In some embodiments, the housing includes an inlet in fluid communication with the air channel and configured to receive pressurized fluid from an air supply and one or more outlets in fluid communication with the air channel and configured to direct the received pressurized fluid toward the beverage container. Moreover, in some embodiments, the inlet is disposed proximate a first end of the housing, and the one or more outlets are disposed on a sidewall of the housing. In some embodiments, the air channel narrows from a direction of the first end of the housing to a direction of a second end of the housing to balance air flow proximate the second end of the housing with air flow proximate the first end of the housing. In addition, in some embodiments, each of the one or more outlets narrows from the direction of the first end of the housing to the direction of the second end of the housing to balance air flow exiting the one or more outlets. In some embodiments, the one or more outlets includes a slot that narrows from the direction of the first end of the housing to the direction of the second end of the housing. Moreover, in some embodiments, the housing is substantially vertical, the direction of the first end of the housing is proximate a bottom of the housing, and the direction of the second end of the housing is proximate a top of the housing.

Also, in some embodiments, the air knife is configured to direct the air flow in a substantially horizontal direction. In some embodiments, the air knife is configured to direct the air flow in a slightly upward or slightly downward direction.

In addition, some embodiments may also include an ultraviolet light configured to emit ultraviolet light toward the beverage container while the beverage container is disposed in the wash chamber. Also, in some embodiments, the ultraviolet light is mounted to the housing of the air knife and the housing of the air knife includes a heat sink formed thereon for discharging heat generated by the ultraviolet light.

In addition, some embodiments may further include an ultraviolet light mounted adjacent to the air knife, the ultraviolet light is configured to emit ultraviolet light directed along a radial extending from the axis of rotation, and the air knife is laterally offset from the ultraviolet light and configured to direct air flow along a flow line that is substantially parallel to the radial.

Other embodiments may include various methods for making and/or using any of the aforementioned constructions.

These and other advantages and features, which characterize the invention, are set forth in the claims annexed hereto and forming a further part hereof. However, for a better understanding of the invention, and of the advantages and objectives attained through its use, reference should be made to the Drawings, and to the accompanying descriptive matter, in which there is described example embodiments of the invention. This summary is merely provided to introduce a selection of concepts that are further described below in the detailed description, and is not intended to identify key or essential features of the claimed subject matter, nor is it intended to be used as an aid in limiting the scope of the claimed subject matter.

BRIEF DESCRIPTION OF THE DRAWINGS

FIG. 15 is a functional top plan view of another beverage container washing system consistent with some embodiments of the invention.

FIG. 16 is a front elevational view of an air knife and ultraviolet light assembly from the beverage container washing system of FIG. 15.

FIG. 17 is a rear elevational view of the air knife and ultraviolet light assembly of FIG. 16.

FIG. 18 is a side elevational view of the air knife and ultraviolet light assembly of FIG. 16.

DETAILED DESCRIPTION

Figure 1:
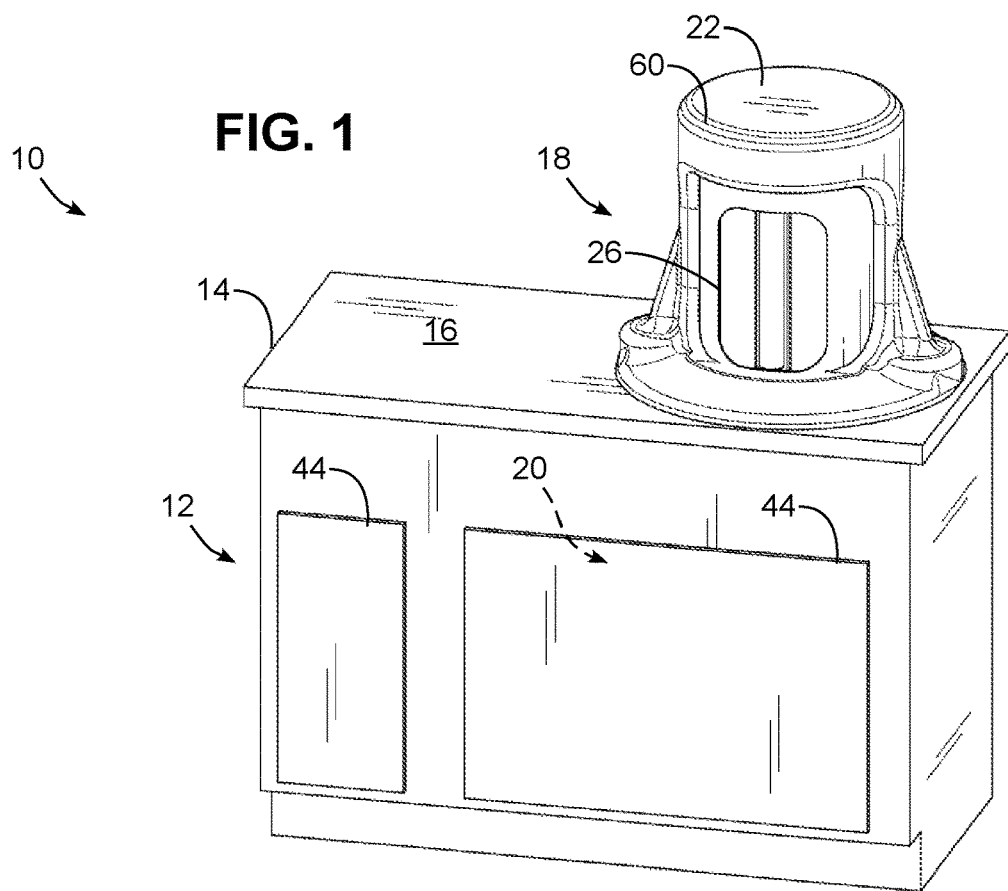
FIG. 1 is a perspective view of a beverage container washing system consistent with some embodiments of the invention.

In some embodiments consistent with the invention, a beverage container washing system may be used to rapidly wash beverage containers, including, for example, reusable beverage containers such as may be provided by customers of a retail establishment.

A beverage container, in this regard, may be considered to be any type of container that is capable of holding a beverage for consumption, including, for example, a cup, a bottle, a bowl, etc. A beverage container may generally include a mouth or opening defined by a lip, and may or may not include a cap, a lid or other form of closure. A beverage container may be reusable to the extent that the beverage container may be reused multiple times, in contrast with a disposable or single use beverage container that is generally thrown away after use.

A beverage container washing system consistent with some embodiments of the invention may be used to wash or clean a beverage container. In some embodiments, a beverage container washing system may also be considered to be a sanitizing system that is also capable of sanitizing a beverage container to inactivate, reduce or destroy microorganisms on the surface of the beverage container, e.g., bacteria and other pathogenic organisms. Sanitization may be achieved through the use of high temperatures, ultraviolet irradiation, disinfecting agents, or some combination of the same, such that a sanitizing operation may be considered to be a particular type of washing operation where some degree of sanitization occurs in addition to washing or cleaning. It will be appreciated, however, that some of the concepts disclosed herein may be utilized in connection with washing systems that, while capable of washing or cleaning a beverage container, are not considered to sanitize the beverage container to the extent required to consider the beverage container as being sanitized at the completion of a washing operation.

It will also be appreciated that a beverage container washing system consistent with the invention may be, but is not necessarily, used in a retail environment (e.g., a bar, a coffee shop, a restaurant, etc.) to rapidly wash the beverage container of a customer prior to filling the beverage container with a beverage that has been purchased by a customer, e.g., in some instances, less than one minute, and in some instances, about 30 seconds or less. Further, a beverage container washing system consistent with the invention may be, but is not necessarily, used to rapidly wash a single, individual beverage container in a washing operation. In other embodiments, for example, some of the concepts disclosed herein may be utilized in non-retail environments, including within a consumer's home, an office environment, or any other environment for which it may be desired to wash beverage containers. Further, even within a retail environment, a washing system consistent with the invention may be used in non-customer facing applications, e.g., behind the counter, in the kitchen, etc. Further, some of the concepts disclosed herein may be adapted for use in connection with washing multiple beverage containers in a single washing operation, as well as washing operations that take one or more minutes to complete.

In the example embodiment discussed hereinafter, hot water (e.g., about 150 degrees/65 degrees Celsius or higher in some embodiments, or about 165 degrees Fahrenheit/74 degrees Celsius or higher in some embodiments), high pressure (e.g., about 100 psi or greater), high speed air for drying, and ultraviolet irradiation are used to rapidly wash and sanitize an individual beverage container, e.g., in about 30 seconds, and do so in a manner that has a minimal countertop space presence. Furthermore, in order to minimize interaction between a customer and retail establishment employee, separate entrance and exit openings are used, such that the opening in which a customer inserts an unwashed beverage container into the system prior to performing a washing operation is different from the opening in which a retail establishment employee removes the washed beverage container at the completion of the washing operation. A washing system consistent with the invention may, in some instances, move the beverage container between multiple stations to perform different actions, and in some instances, operate on different beverage containers concurrently in different stations. In other instances, a washing system consistent with the invention may perform all of the actions associated with a washing operation while the beverage container is maintained in the same location. It will be appreciated, however, that in other embodiments, a washing system consistent with the invention may use the same opening for insertion and removal of a beverage container, and may operate on multiple beverage containers at the same time. Further, in some embodiments, lower temperatures and/or pressures may be used, and ultraviolet irradiation and/or drying may be omitted, or additional actions, such as the introduction of detergents, disinfecting agents, etc. may be used. Therefore, the invention is not limited to the specific embodiments disclosed herein.

Further details regarding various components and features that may be implemented in a beverage container washing system consistent with the invention are also described in U.S. patent application Ser. No. 17/490,884 and U.S. patent application Ser. No. 17/490,888, which were filed on Sep. 30, 2021 by Digman et al. and Boyer et al., are assigned to the same assignee as the present application, and which are incorporated by reference herein.

Beverage Container Washing System

Now turning to the drawings, wherein like parts are denoted by like numbers throughout the several views, FIG. 1 illustrates a beverage container washing system or apparatus 10 consistent with some embodiments of the invention, and suitable for installation, for example, in a cabinet 12 that forms a counter 14 in a retail establishment. In the illustrated embodiment, washing system 10 may also be considered to be a sanitizing system 10 due to the use of hot water and/or ultraviolet irradiation, so these terms may be used interchangeably. It will be appreciated, however, that the reference to a particular concept used in a sanitizing system or in connection with a sanitizing operation does not necessarily mean that the concept cannot also be used in washing system or in connection with washing operations that are not necessarily considered sufficient for full sanitization of a beverage container.

Counter 14 includes a countertop 16, and washing system 10 includes a countertop portion 18 that projects above countertop 16 and an undercounter portion 20 that is predominantly mounted within cabinet 12 to minimize the amount of countertop space occupied by countertop portion 18. In other embodiments, washing system 10 may be fully implemented in a countertop, standalone or undercounter configuration, so the invention is not limited to the particular combination of countertop and undercounter portions as illustrated herein. In some embodiments, the countertop portion may be fixed to a countertop, but the undercounter portion may be separated, or may be mounted on a cart to simplify installation and service.

Figure 2:
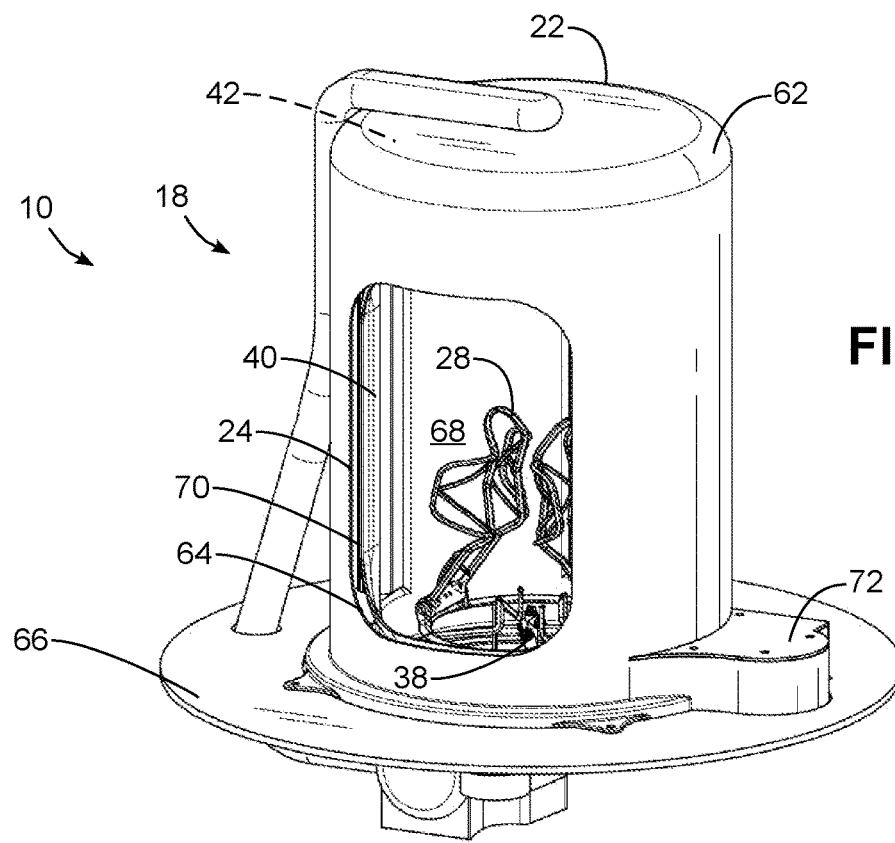
FIG. 2 is a perspective view of an opposite side of a countertop portion of the beverage container washing system of FIG. 1.

With additional reference to FIG. 2, which shows an opposite side of countertop portion 18 of washing system 10, the countertop portion 18 generally includes a housing 22 having a pair of openings 24, 26, with opening 24 operating as an entrance through which a beverage container is inserted or received prior to performing a washing operation and opening 26 operating as an exit through which a beverage container is accessed or removed after performing a washing operation. Through the use of separate openings 24, 26, handling of unwashed beverage containers by retail establishment employees may be reduced or eliminated. In other embodiments, however, a single entrance/exit opening may be used.

Countertop portion 18 also includes a holder 28 that is disposed within housing 22 and is configured to hold a beverage container during a washing or sanitizing operation. In addition, and with additional reference to FIG. 3, a number of assemblies 30, 32, 34 are also utilized for performing various actions on the beverage container during a washing or sanitizing operation, and are controlled by a controller 36, which will be discussed in greater detail below.

First, a spray assembly 30, including one or more sprayers (e.g., sprayer 38 as shown in FIG. 2) is disposed within housing 22 and configured to spray a wash fluid onto the beverage container while the beverage container is held by holder 28. The wash fluid may be water in some instances, while in other instances, the wash fluid may include various agents such as detergents, disinfecting agents, etc. As will become more apparent below, when sanitization is desired, the wash fluid sprayed by the spray assembly 30 may be heated to a sanitizing temperature, e.g., about 150 degrees Fahrenheit or higher in some embodiments, and about 165 degrees Fahrenheit or higher in some embodiments, and in some instances may be pressurized at a high pressure, e.g., about 100 psi or above. Second, an ultraviolet sanitizing assembly 32, including one or more ultraviolet lights 40 (one of which is shown in FIG. 2), is disposed within housing 22 and configured to emit ultraviolet light toward the beverage container while the beverage container is held by holder 28. Third, a dryer assembly 34, e.g., including one or more air outlets 42, is disposed within housing 22 and configured to blow air onto the beverage container while the beverage container is held by holder 28. A number of other components in each of these assemblies, as noted above, may be disposed within cabinet 12, and may be accessed, for example, through one or more cabinet doors 44 (FIG. 1).

Figure 3:
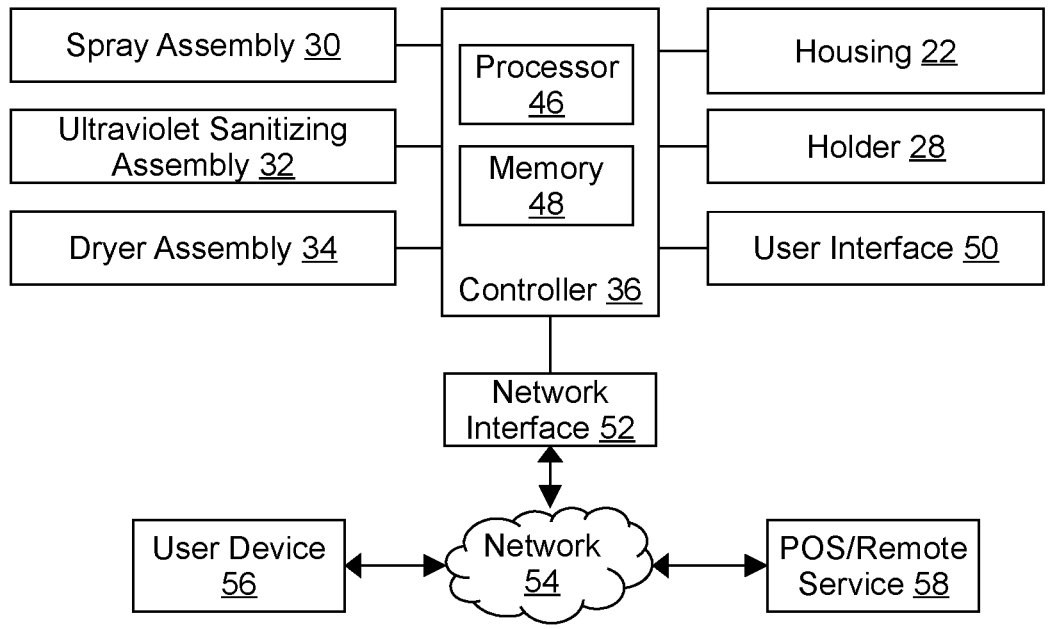
FIG. 3 is a block diagram of an example control system for the beverage container washing system of FIG. 1.

Now turning specifically to FIG. 3, washing system 10 may be under the control of a controller 36 that receives inputs from a number of components and drives a number of components in response thereto. Controller 36 may, for example, include one or more processors 46 and a memory 48 within which may be stored program code for execution by the one or more processors 46. The memory may be embedded in controller 36, but may also be considered to include volatile and/or non-volatile memories, cache memories, flash memories, programmable read-only memories, read-only memories, etc., as well as memory storage physically located elsewhere from controller 36, e.g., in a mass storage device or on a remote computer interfaced with controller 36. Controller 36 may also be implemented as a microcontroller in some embodiments, and as such these terms are used interchangeably herein. Controller 36 may also include discrete circuit logic in some embodiments, e.g., including passive and/or active circuit components.

As shown in FIG. 3, controller 36 may be interfaced with various components, including a spray assembly 30, ultraviolet sanitizing assembly 32, and dryer assembly 34, as well as housing 22 and/or holder 28. In addition, one or more user interfaces 50, e.g., including various input/output devices such as knobs, dials, sliders, switches, buttons, lights, textual and/or graphics displays, touch screen displays, speakers, image capture devices, microphones, etc., may be used for receiving input from and communicating with one or more users. Separate user controls and/or displays may be provided, for example, on or near housing 22 for a customer and a retail establishment employee (e.g., to start or stop a washing operation), and in some instances, additional controls and/or displays may be provided at different locations, e.g., under countertop 16 or behind a cabinet door 44, to perform additional operations, such as initializing and/or shutting off the system, flushing the system, displaying error conditions, etc.

In some embodiments, controller 36 may also be coupled to one or more network interfaces 52, e.g., for interfacing with external devices via wired and/or wireless networks 54 such as Ethernet, Bluetooth, NFC, cellular and other suitable networks. It may be desirable, for example, to interface with one or more user devices 56, e.g., a customer's mobile phone, to enable a customer to start a washing operation, in some instances in connection with ordering and/or paying for a beverage. It may also be desirable to interface with various backend devices such as a point of sale (POS) system and/or a remote service 58. Moreover, in some embodiments, at least a portion of controller 36 may be implemented externally, e.g., within a mobile device, a cloud computing environment, etc., such that at least a portion of the functionality described herein is implemented within the portion of the controller that is externally implemented.

In some embodiments, controller 36 may operate under the control of an operating system and may execute or otherwise rely upon various computer software applications, components, programs, objects, modules, data structures, etc. In addition, controller 36 may also incorporate hardware logic to implement some or all of the functionality disclosed herein. Further, in some embodiments, the sequences of operations performed by controller 36 to implement the embodiments disclosed herein may be implemented using program code including one or more instructions that are resident at various times in various memory and storage devices, and that, when read and executed by one or more hardware-based processors, perform the operations embodying desired functionality. Moreover, in some embodiments, such program code may be distributed as a program product in a variety of forms, and that the invention applies equally regardless of the particular type of computer readable media used to actually carry out the distribution, including, for example, non-transitory computer readable storage media. In addition, it will be appreciated that the various operations described herein may be combined, split, reordered, reversed, varied, omitted, parallelized and/or supplemented with other techniques known in the art, and therefore, the invention is not limited to the particular sequences of operations described herein.

As noted above, controller 36 may be interfaced in some embodiments with one or both of housing 22 and holder 28. In the embodiment illustrated in FIGS. 1-2, for example, washing system 10 includes a concentric housing arrangement, also referred to herein as a concentric dome arrangement, whereby housing 22 includes an outer decorative cover 60 coupled with a pair of concentric housing members or domes 62, 64 supported by a base 66. Concentric housing member or dome 62 is an outer concentric housing member or dome while concentric housing member or dome 64 is an inner concentric housing member or dome that is disposed inwardly from outer concentric housing member or dome 62 and forms at least a portion of a wash chamber 68 with the base. Entrance opening 24 and exit opening 26 are defined in outer concentric housing member 62 while an additional opening 70 is provided in inner concentric housing member 64, and a drive motor 72 is used to rotate inner concentric housing member 64 to selectively move opening 70 between a loading position where opening 70 is aligned with entrance opening 24 to provide access to the wash chamber for insertion of the beverage container prior to a washing operation, a washing position where opening 70 is intermediate entrance and exit openings 24, 26 (thereby closing both openings), and an unloading position where opening 70 is aligned with exit opening 26 to provide access to the wash chamber for removal of the beverage container at the completion of a washing operation.

In other embodiments, however, no mechanical manipulation of a housing may be used, whereby controller 36 may not be electronically coupled to housing 22. For example, it may be desirable in some embodiments to keep an entrance opening and an exit opening open at all times, or to use a door or other manually or mechanically actuated closure.

In the illustrated embodiment of FIGS. 1 and 2, holder 28 may be fixed in location and thus no electronic coupling between controller 36 and holder 28 may be used. In other embodiments, however, it may be desirable to configure holder 28 to electronically open or close, rotate, and/or move, including moving between different stations, so controller 36 may be electronically coupled to holder 28 in some embodiments.

Figure 4:
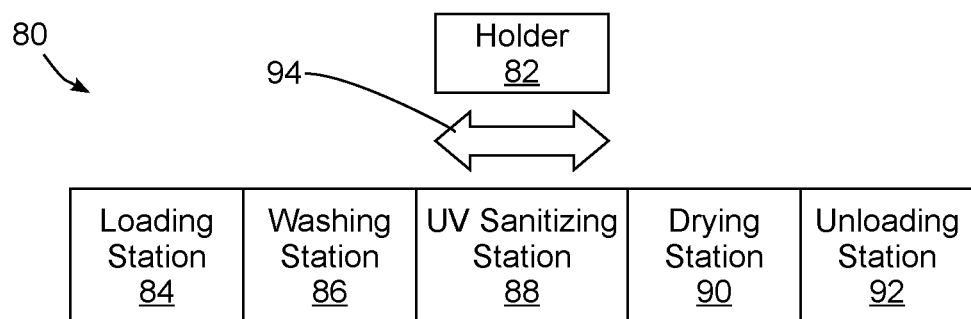
FIG. 4 is a block diagram of an alternate beverage container washing system to that of FIG. 1.

For example, as illustrated by washing system 80 of FIG. 4, a holder 82 may be moved between different stations, e.g., a loading station 84, a washing station 86, an ultraviolet sanitizing station 88, a drying station 90 and/or an unloading station 92, e.g., by a conveyor 94 or other articulating configuration. Further, in some embodiments, multiple actions may be performed at the same station (e.g., drying and exposing to ultraviolet radiation in the same station), or multiple stations may perform different aspects of a particular action (e.g., separate wash and rinse stations).

Figure 5A:
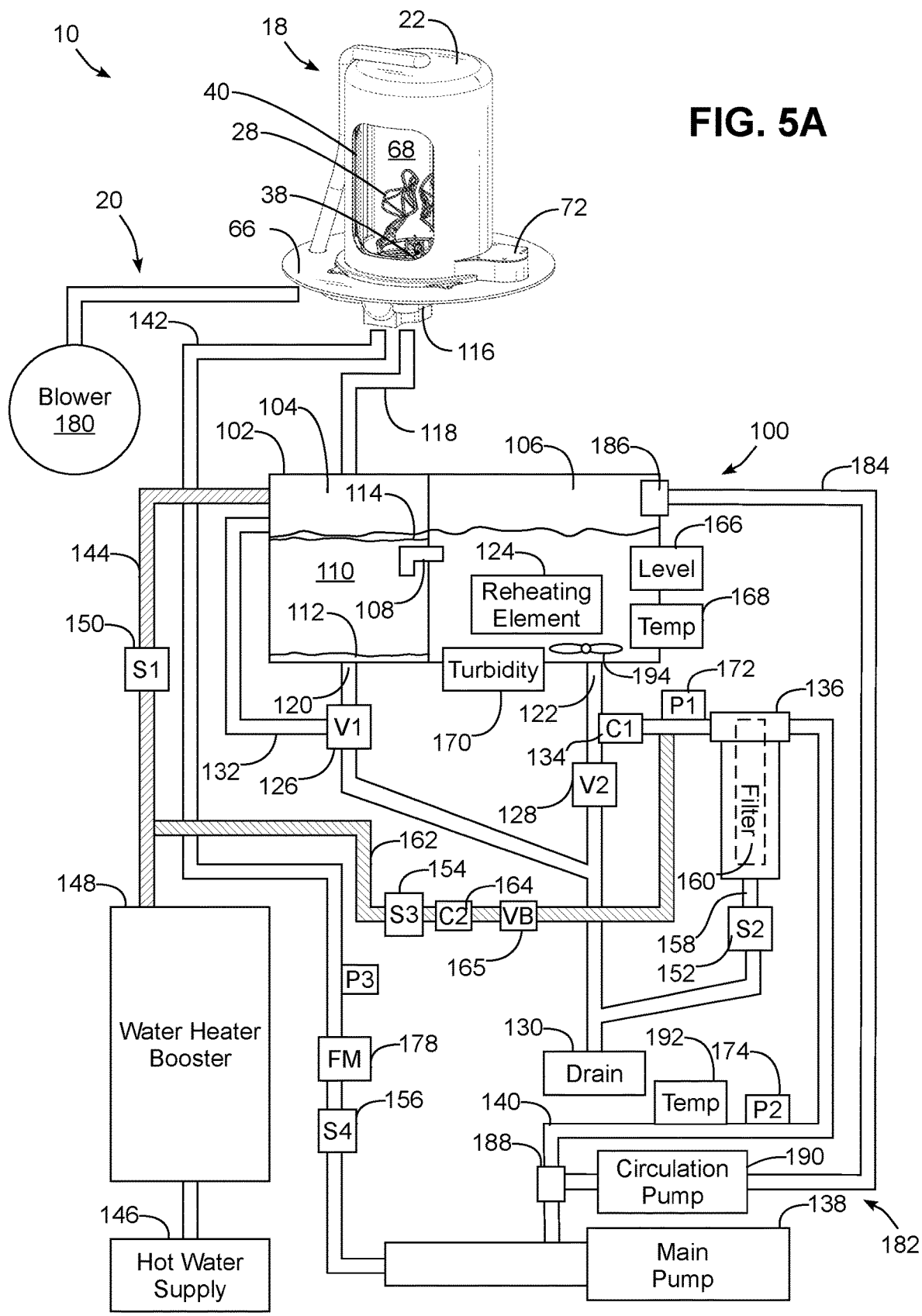
FIG. 5A is a block diagram of an example undercounter portion of the beverage container washing system of FIG. 1.

Now turning to FIG. 5A, and as discussed above, beverage container washing system 10 includes a number of additional components, many of which are in an undercounter portion 20, that operate each of spray assembly 30, ultraviolet sanitizing assembly 32 and dryer assembly 34. Spray assembly 30, for example, additionally includes a wash fluid recirculation assembly 100 that is disposed in cabinet 12 and underneath countertop 16 and is in fluid communication with sprayer 38 through countertop 16.

In particular, in the illustrated embodiment, it is desirable to recirculate wash fluid for use in multiple washing operations to reduce overall water and energy consumption. Rather than utilizing fresh water for each washing operation, the wash fluid may be reused for multiple washing operations, and in some instances, one or more fluid property sensors (e.g., a turbidity sensor and/or a conductivity sensor) may be used to monitor the state of the wash fluid and periodically perform a wash fluid refresh operation to drain at least a portion of the wash fluid to a drain and replace the removed portion with fresh water (referred to herein as make up water).

Wash fluid recirculation assembly 100, in particular, includes a tank 102 including first and second chambers 104, 106 with a cross-over 108 that fluidly couples first and second chambers 104, 106 to one another. First chamber 104 is generally used to house black water, while second chamber 106 is used to generally house gray water. Cross-over 108 may be implemented as an inverted conduit that is disposed below the fluid level of the wash fluid 110 disposed in tank 102, which generally reduces the amount of solid particles 112 (which generally fall to the bottom of first chamber 104 and thus below the inlet of the inverted conduit) and floating particles 114 (which generally float in first chamber 104 and thus above the inlet of the inverted conduit) that are drawn into second chamber 106. A collector 116 in base 66 of housing 22 collects wash fluid sprayed by sprayer 38, and the collected wash fluid is conveyed by a collector line 118 to first chamber 104 of tank 102.

Each chamber 104, 106 has an associated drain or outlet 120, 122, and tank 102 further includes a heater 124, e.g., a reheating element, that maintains the temperature of wash fluid 110 above the desired sanitizing temperature. Respective drain devices such as dump valves 126, 128 (also referred to as valves V1 and V2) are coupled to outlets 120, 122 and feed to a drain 130, e.g., in the building plumbing system. Dump valve 126 in some embodiments may also include an overflow line 132 to collect wash fluid when the fluid level rises above a predetermined level. In some embodiments, drain devices other than valves may be used in other embodiments, e.g., drain pumps, and in some embodiments, overflow may be controlled by a separate float that activates a drain pump.

A check valve 134 (also denoted as C1) is coupled between outlet 122 and dump valve 128 to route wash fluid to a filter 136 and then onward to a pump 138 through a recirculation line 140, and pump 138 pressurizes the wash fluid (e.g., to a pressure about 100 psi or above in some embodiments, and in some embodiments about 150 psi or above) and outputs the pressurized wash fluid to sprayer 38 through a sprayer supply line 142. In some embodiments, pump 138 may be a multi-stage pump, e.g., 1 hp, 17-stage pump. During a washing operation, wash fluid in the second chamber 106 of tank 102 is thus drawn out of outlet 122 and through filter 136 by pump 138, and then pressurized and supplied to sprayer 38 by pump 138. The wash fluid emitted by sprayer 38 is then collected in collector 116 of base 66 and returned to first chamber 104 of tank 102.

Fresh or make up water is supplied to tank 102 by a make up water line 144. In order to supply the fresh or make up water at a suitable temperature for washing or sanitizing operations, fresh water from a hot water supply 146 (e.g., output by a building water heater) may first be passed through a water heater booster 148, which maintains a quantity of water at an elevated temperature (e.g., about 150 degrees Fahrenheit or higher in some embodiments, and about 165 degrees Fahrenheit or higher in some embodiments). In other embodiments, however, fresh water may be supplied from a cold water supply and heated by water heater booster, and in some embodiments, water heater booster 148 may be omitted, with the temperature of the wash fluid in tank 102 predominantly controlled by reheating element 124.

Four additional valves, e.g., solenoid valves 150, 152, 154 and 156 (also denoted respectively as valves S1-S4), may also be incorporated into assembly 100. Valve 150 is a make up water valve, and is provided in make up water line 144 to control the supply of make up water to first chamber 104 of tank 102. Valve 156 is disposed in sprayer supply line 142, and is actuated when pump 138 is actuated to supply wash fluid to sprayer 38.

In addition, in the illustrated embodiment, filter 136 is a flushable filter and includes a second, cleanout outlet 158, and valve 152 is configured as a cleanout valve that couples cleanout outlet 158 to drain 130. Valve 154 in turn is configured as a filter clean valve that is coupled to make up water line 144 to supply fresh water to recirculation line 140 upstream of a filter element 160 of filter 136 through a fresh water supply line 162. It will be appreciated that when valves 152, 154 are closed and pump 138 is running wash fluid from tank 102 flows through an upstream portion of recirculation line 140, through filter element 160, and through the first outlet of the filter and a downstream portion of the recirculation line 140 to pump 138. However, whenever it is desirable to perform a filter cleaning operation (generally while pump 138 is shut off), valves 152 and 154 may be opened to supply fresh water to an outside or upstream side of the filter element 160 and then out cleanout outlet 158 to run fresh water over the outside of the filter element and flush any debris on the filter element into drain 130. In addition, in some embodiments, a check valve 164 (also denoted as C2) and a vacuum breaker 165 may also be provided in fresh water supply line 162 to inhibit reverse fluid flow to the make up water line 144. In other embodiments, gray water may be used to clean the filter, e.g., by coupling line 162 to an outlet of pump 138 instead of to a fresh water source, e.g., between pump 138 and valve 156, and with an additional valve controlling fluid flow through line 162.

Assembly 100 may also include a number of sensors to monitor the operation of the assembly and initiate various actions in response thereto. A fluid level sensor 166 may be disposed in tank 102 to sense a fluid level therein, and the controller may utilize the output of this sensor to control make up water valve 150 to maintain a desired fluid level in the tank. A temperature sensor 168 may be disposed in tank 102 to sense the wash fluid temperature, and the controller may utilize the output of this sensor to control reheating element 124 to regulate the wash fluid temperature in the tank. One or more fluid property sensors, e.g., a turbidity sensor 170, a conductivity sensor, and/or another sensor suitable for measuring various fluid properties, may also be disposed in tank 102, e.g., in second chamber 106, or otherwise disposed elsewhere in assembly 100, to sense the water quality and/or cleanliness of the wash fluid, and the controller may utilize the output of this sensor to trigger a wash fluid refresh operation that drains at least a portion of the wash fluid to drain 130 and adds fresh water to tank 102.

A pair of pressure sensors 172, 174 (also denoted as P1 and P2) may also be disposed upstream and downstream of filter element 160 (e.g., within upstream and downstream portions of recirculation line 140), and the controller may utilize the outputs of these sensors to sense a pressure differential indicative of a dirty or clogged filter element, and thereby trigger a filter cleaning operation. An additional pressure sensor 176 (also denoted as P3) and a flowmeter 178 may also be disposed downstream of pump 138, e.g., in sprayer supply line 142, and the controller may use the outputs of these sensors to monitor the supply of wash fluid to sprayer 38. As will also be discussed in greater detail below, a dryer assembly may also include one or more blowers, e.g., a blower 180, that supply air to one or more air knives.

Figure 6A:
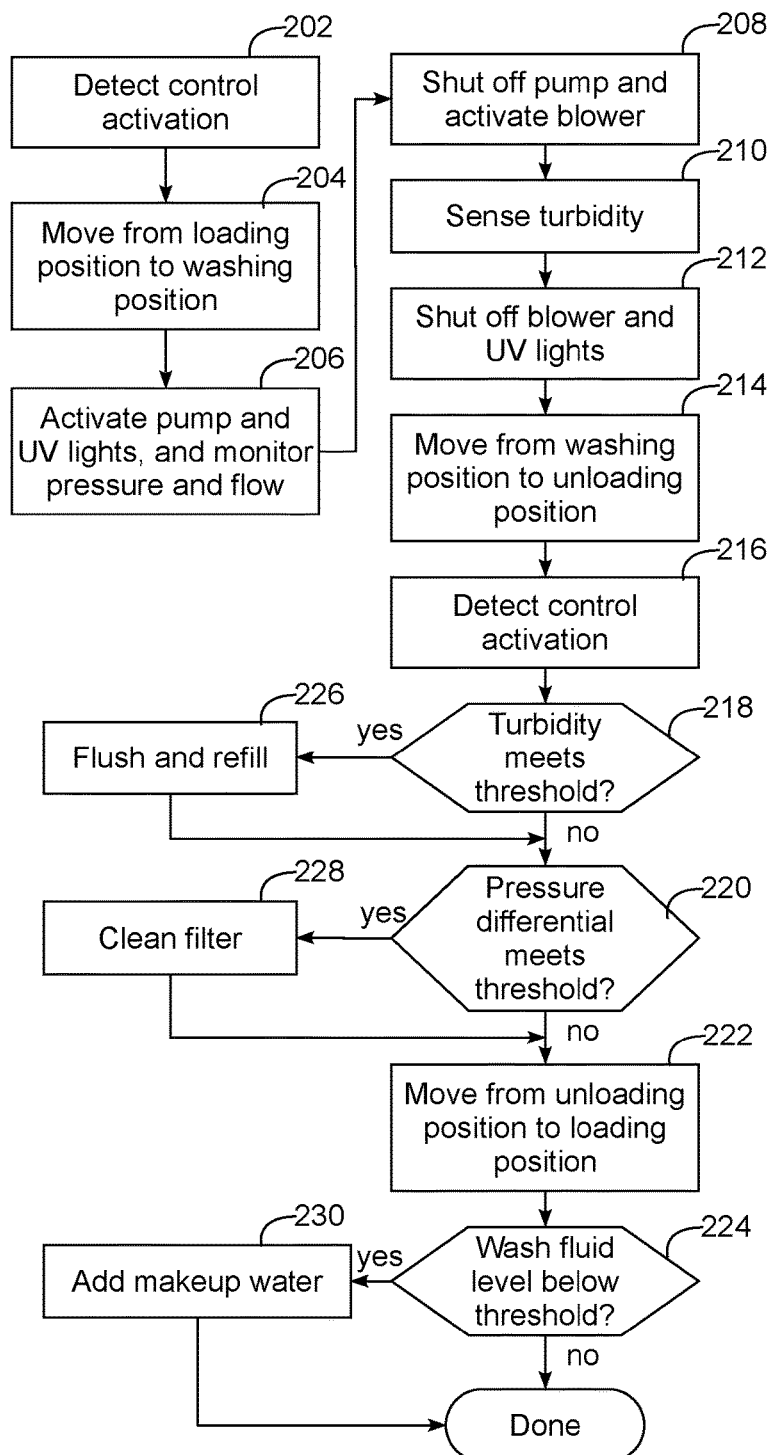
FIG. 6A is a flowchart illustrating an example sequence of operations for a washing operation performed by the beverage container washing system of FIG. 1.

FIG. 6A next illustrates an example sequence of operations 200 capable of being performed by controller 36 of beverage container washing system 10 to perform washing operations in a manner consistent with some embodiments of the invention. It is assumed that washing system 10 includes three positions, a loading position where the washing system is configured to allow a customer to insert a beverage container into the holder in the wash chamber (e.g., through entrance opening 24 of FIG. 2), a washing position where the washing system is configured to perform a washing operation (e.g., with entrance and exit openings 24, 26 closed), and an unloading position where the washing system is configured to allow an employee to remove a beverage container from the holder in the wash chamber (e.g., through exit opening 26 of FIG. 1). It is also assumed that at the beginning of sequence 200, the washing system 10 is in the loading position, and a customer has inserted a beverage container into the holder in the wash chamber. In addition, it will be appreciated that during this time, reheating element 124 (e.g., as a result of a background process executing in a controller, or in a dedicated circuit) may also be cycled to maintain the fluid temperature in the tank at a desired level.

Sequence 200 may be initiated, for example, in response to selection of a "start" control by a customer or employee, e.g., on a physical user interface provided on the washing system, via a foot pedal or switch, via a gesture or audible command, on a display of a POS system, on an app running on a mobile device, or another suitable manner for starting a washing operation. In block 202, activation of the control is detected, and in block 204, the washing system is moved from the loading position to the washing position (e.g., by rotating inner concentric housing member 64 with drive motor 72).

Next, in block 206, the pump of the spray assembly and the UV lights of the ultraviolet sanitizing assembly are activated to initiate spraying of the beverage container by sprayer 38 and irradiation of the beverage container with ultraviolet light (in another embodiment, the spray assembly and UV lights may be activated sequentially rather than concurrently). In addition, during this time pressure sensors 172-176 and flowmeter 178 are monitored to track the output flow of pump 138, as well as to monitor the pressure differential on the upstream and downstream sides of filter 136.

After some period of time, the pump is shut off and blower 180 of the dryer assembly is activated in block 208 to transition between washing the beverage container and drying the beverage container. Then, in block 210, the turbidity (or another property of the wash fluid) is sensed using sensor 170, and thereafter, the blower and UV lights are shut off in block 212, whereby the washing or sanitizing operation is complete.

Next, in block 214, the washing system is moved from the washing position to the unloading position (e.g., by rotating inner concentric housing member 64 with drive motor 72) to enable the beverage container to be removed from the holder in the wash chamber. Confirmation of removal of the beverage container is obtained in block 216 by detecting activation of an appropriate control (e.g., the same control used to start the washing operation in block 202 or a different control). Blocks 218 and 220 then determine whether conditions were detected indicating the need for either or both of a wash fluid refresh operation and a filter clean operation, and if neither operation is needed, control passes to block 222 to move the washing system from the unloading position to the loading position (e.g., by rotating inner concentric housing member 64 with drive motor 72) to prepare the washing system for a next washing operation. It will be appreciated that in embodiments where the loading and unloading positions are the same, block 222 may be omitted. Block 224 then determines, e.g., using fluid level sensor 166, whether the wash fluid level in the tank is below a threshold (e.g., where the wash fluid level has dropped below a minimum level), and assuming not, performance of sequence 200 is complete.

Returning to block 218, this block determines whether a need exists for a wash fluid refresh operation by determining if the turbidity sensed in block 210 (or another sensed fluid property) meets a threshold, e.g., where the turbidity of the wash fluid exceeds a level for which it is desired to flush at least a portion of the wash fluid from the tank and replace it with fresh water. If so, block 218 passes control to block 226 to perform a wash fluid refresh operation. In such an operation, one or both of dump valves 126 and 128 (or drain pumps, if used) may be actuated to drain at least a portion of the wash fluid in tank 102, and make up water valve 150 may be actuated to add make up water to the tank. In addition, during such an operation the filter may be cleaned concurrently with the flushing and refilling of wash fluid in some embodiments.

In one example embodiment, a wash fluid refresh operation may incorporate the following sequence of actions:
1. Position washing system in wash position
2. Open valve 126 (V1) and valve 152 (S2)
3. Wait 3 Sec
4. Open valve 128 (V2)
5. Wait 3 Sec
6. Open valve 154 (S3) and valve 150 (S1)
7. Wait 5 Sec
8. Close valve 126 (V1) and valve 152 (S2)
9. Wait 5 Sec
10. Close valve 154 (S3)
11. Wait 10 Sec
12. Close valve 128 (V2)
13. Fill until fluid level sensor 166 indicates full tank 14. Run pump 138 for 10 Sec
15. Wait 5 Sec
16. Recheck turbidity, and if turbidity is below threshold, return washing system to load position for next washing operation, otherwise repeat steps 1-16

It will be appreciated that other sequences may be used in other embodiments. Moreover, while in some embodiments a wash fluid refresh operation may replace all wash fluid with fresh water, in other embodiments only a portion of the wash fluid may be flushed and replaced with fresh water.

Returning to block 220, the block determines whether a need exists for a filter cleaning operation by determining if the pressure differential between pressure sensors 172, 174 meets a threshold, e.g., a pressure differential greater than some threshold that indicates that fluid flow through the filter has been impeded to an extent that cleaning of the filter is desirable. If so, block 220 passes control to block 228 to clean the filter, e.g., by actuating cleanout valve 152 and filter clean valve 154 to run fresh water over the outer surface of the filter element.

In one example embodiment, a filter cleaning operation may incorporate the following sequence of actions:
1. Open valve 152 (S2)
2. Wait 3 Sec
3. Open valve 154 (S3) for 5 seconds and then close
4. Wait 3 Sec
5. Close valve 152 (S2)
6. Check wash fluid level and fill as needed Returning to block 224, the block determines whether a need exists to add make up water to the tank by determining if the wash fluid level sensed by fluid level sensor 166 meets a threshold, e.g., is below a minimum fluid level. If so, block 224 passes control to block 230 to actuate make up water valve 150 to add makeup water, until the fluid level sensor indicates that the tank is full, whereby valve 150 may be shut off. In some embodiments, block 224 may be performed at the same time as blocks 218 and 220; however, it may be desirable to defer block 224 to allow for wash fluid in the wash chamber to have time to fully drain into the tank before checking the fluid level in the tank.

It will be appreciated that, assuming none of the supplemental operations of blocks 226, 228 and 230 are required, the bulk of the runtime of a washing operation is occupied by the washing, UV sanitizing and drying actions performed in blocks 206-212, and it will also be appreciated that the UV sanitizing action overlaps in time with each of the washing and drying actions, such that, for example, if the washing action takes X seconds and the drying action takes Y seconds, the UV sanitizing action takes Z=X+Y seconds. In other embodiments, particularly where a holder is moved between multiple stations, however, the UV sanitizing action may overlap only a portion of one or both of the washing and drying actions, or may not overlap with either of the washing and drying actions at all. In addition, it will be appreciated that moving between the loading, washing, and unloading positions may also occupy some time within a washing operation in some embodiments. It may be desirable in some embodiments, for example, to provide a washing operation having a duration of about 45 seconds or less, with, for example, about 5 seconds used to move from the loading position to the washing position, about 30 seconds for the washing action, about 5 seconds for the drying action, about 30 seconds for the UV sanitizing action (concurrent with the washing action, or alternatively in another embodiment about 35 seconds concurrently with both the washing and drying actions), and about 5 seconds to move from the washing position to the unloading position.

It will be appreciated that washing system 10 may vary in other embodiments in a number of manners. For example, an additional filter may be used in first chamber 104 of tank 102 in some embodiments to filter wash fluid before it is transferred to second chamber 106. Further, in some embodiments, a separate rinse action may be performed using a source of fresh water after the washing action. Further, in some embodiments, one or more disinfecting agents, e.g., various hypochlorite sanitizing compositions, may be introduced into tank 102 and maintained at a minimum level based upon sensing by a suitable sensor. In addition, further operations, such as startup operations that initialize the washing system, and shutdown operations that flush the washing system and shut down all components, may also be supported.

It may also be desirable in some embodiments to incorporate a heated wash fluid circulation system into a beverage container washing system in order to maintain a desired temperature of wash fluid at the ready for a next wash cycle. In particular, it has been found that significant temperature discrepancies may exist in various locations in a washing system, particularly when the washing system has not been used for some period of time. Given the desirability of performing a washing action in 30 seconds or less in some embodiments, as well as the desirability of relying on the heat of the wash fluid to sanitize a utensil (e.g., using a wash fluid at a sanitizing temperature of about 150 degrees Fahrenheit or higher in some embodiments, and about 165 degrees Fahrenheit or higher in some embodiments), it is generally desirable for the wash fluid emitted by the sprayer 38 to be at the desired sanitizing temperature as soon as possible after the washing action has been initiated. However, even as the wash fluid in tank 100 is maintained at the desired sanitizing temperature by heater 124, a not-insignificant quantity of wash fluid may nonetheless be retained in the components that are intermediate tank 100 and sprayer 38, including, but not limited to filter 136, main pump 138, recirculation line 140, and sprayer supply line 142, such that at the initiation of a washing action through activation of main pump 138, the wash fluid retained in those components will flow through the components and be emitted by the sprayer prior to the wash fluid maintained at the desired temperature in tank 100 ever reaches the sprayer. Thus, if the wash fluid retained in the intermediate components is allowed to cool, e.g., as a result of non-use of the washing system for some period of time, it may take several seconds for the fluid maintained at the desired temperature in the tank to reach the sprayer so that the utensil being washed is being sprayed with wash fluid at the desired temperature.

Furthermore, non-use of a washing system for some period of time may also, in some instances, allow for temperature discrepancies to develop in different levels of tank 100, such that even some of the wash fluid that is retained in the tank may not be at the desired temperature when a washing action is initiated.

As a result of these discrepancies, the duration of a washing action may need to be extended to ensure that a sufficient duration of spraying at the desired sanitizing temperature is achieved, otherwise washing performance may be inconsistent depending upon how long the washing system has remained in an idle state.

In order to address these issues, in some embodiments of the invention it may be desirable to incorporate a heated wash fluid circulation system into a beverage container washing system in order to circulate heated wash fluid in one or more lines intermediate the tank and the sprayer of the washing system in order to maintain a desired wash fluid temperature within the one or more lines.

Returning to FIG. 5A, for example, it may be desirable to incorporate a heated wash fluid circulation system 182 into beverage container washing system 10, e.g., to circulate wash fluid in one or more lines between tank 102 and sprayer 38 back to tank 102 to be heated by heater 124 disposed therein, at least during at least a portion of the time that main pump 138 is idle. In this embodiment, for example, and as noted above, sprayer 38 is supplied with wash fluid from tank 102 through a recirculation line 140 that is coupled to a low pressure side of a main pump 138 that pressurizes the wash fluid and supplies the pressurized wash fluid to the sprayer 38 through a sprayer supply line 142. Also in this embodiment, the heated wash fluid circulation system 182 includes a return line 184 that is coupled between an inlet 186 of tank 102, e.g., in chamber 106 thereof, and recirculation line 140, e.g., through a tee fitting 188. A circulation pump 190 is coupled to return line 184 and, when activated, draws wash fluid from recirculation line 140 through tee fitting 188 into return line 184, and conveys the wash fluid back to tank 102 through inlet 186. In addition, heated wash fluid from tank 102 is drawn into recirculation line 140 and through filter 136 (which is upstream of return line 184), thereby enabling the wash fluid in recirculation line 140 to be maintained at a relatively constant temperature that in some instances may be substantially equal to the temperature of the wash fluid in the tank, or in some instances at a somewhat reduced temperature based upon heat loss through the recirculation line while the circulation pump is active.

It will be appreciated that various factors such as the flow rate or pressure of the circulation pump and/or the amount of insulation (if any) used on the recirculation line may affect the degree of heat loss that occurs during circulation, and that, for example, the temperature setpoint for tank 102 may be controlled in some embodiments to account for the expected heat loss, such that a temperature in the recirculation line is maintained at a suitable sanitizing temperature if desired. In some embodiments, a temperature sensor 192 may be coupled to return line 184, or alternatively to recirculation line 140 and/or sprayer supply line 142, to enable the wash fluid temperature to be monitored, and in some instances, controlled to a predetermined setpoint.

It may also be desirable in some embodiments to also include a mixer 194 in tank 102 (e.g., in chamber 106) to stir wash fluid in the tank and thereby reduce temperature variations within the tank. In some embodiments, mixer 194 may be a magnetic mixer, although in other embodiments, a mechanical mixer or other suitable mechanism for stirring or agitating the wash fluid in tank 102 may be used.

In the embodiment of FIG. 5A, return line 184 is coupled to recirculation line 140 proximate the low pressure or suction side of main pump 138, such that a majority of the length of recirculation line 140 is within the closed circuit formed with return line 184, thereby maximizing an amount of wash fluid in recirculation line 140 that is circulated back to the tank and heated, and minimizing an amount of wash fluid in recirculation line 140 that is allowed to cool at the low pressure side of the main pump. It will be appreciated, however, that in other embodiments, return line 184 may be coupled to recirculation line 140 at different points along its length, and in some instances upstream of one or more components illustrated as being coupled to recirculation line 140, e.g., various pressure switches, valves, filters, fittings, etc. In addition, in some embodiments return line 184 may be coupled to another line that couples tank 102 to sprayer 38, e.g., sprayer supply line 142, and thus may be coupled to the downstream, or high pressure side of main pump 138. In some embodiments, return line 184 (or multiple return lines) may couple to multiple points in the washing system to circulate wash fluid back to tank 102 for heating.

Figure 5B:
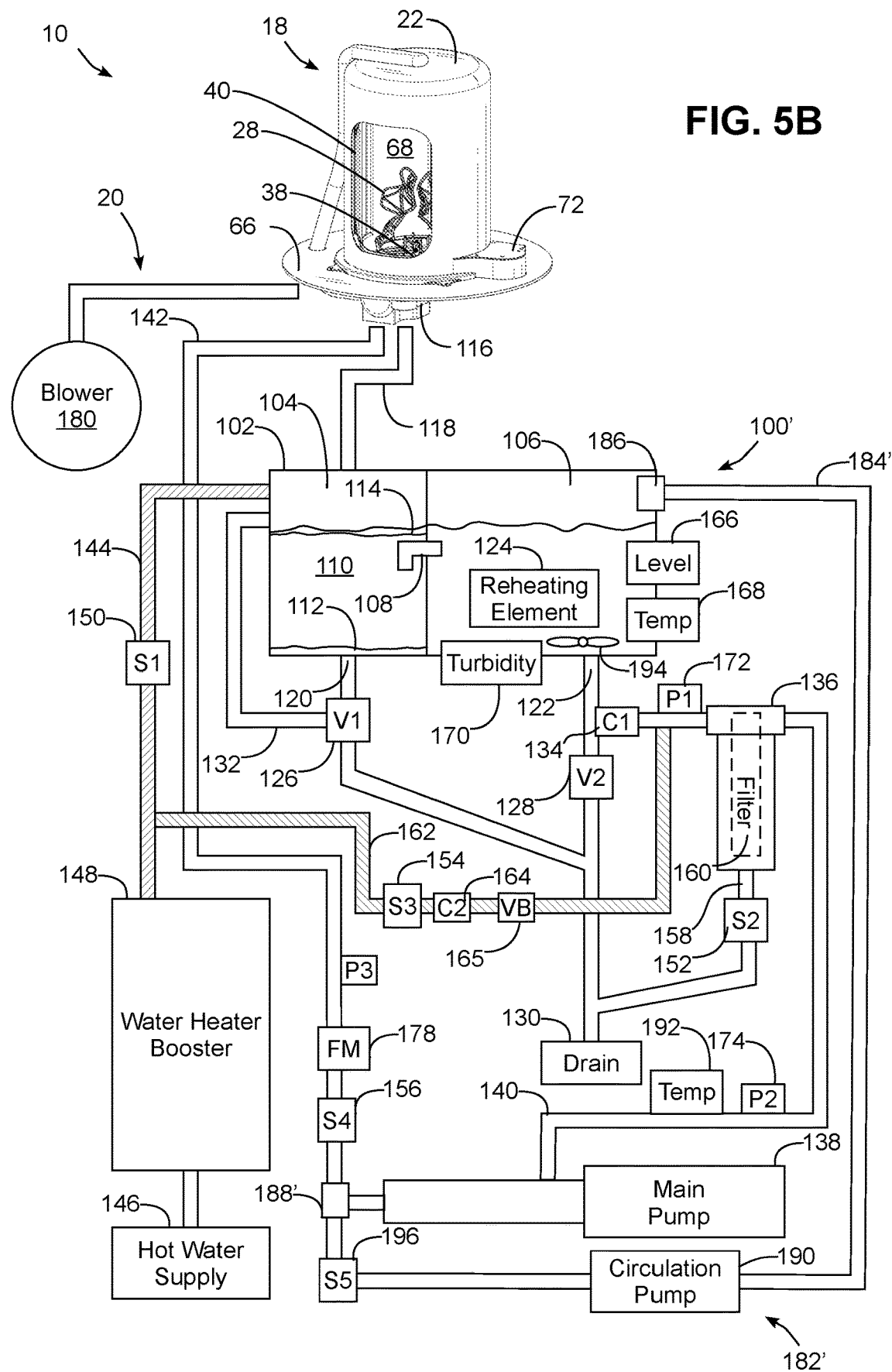
FIG. 5B is a block diagram of another example undercounter portion of the beverage container washing system of FIG. 1.

As one specific example, FIG. 5B illustrates an alternate wash fluid recirculation assembly 100' suitable for use in beverage container washing system 10, and including a heated wash fluid circulation system 182' that includes a return line 184' that, rather than being coupled to the low pressure side of main pump 138, is coupled to sprayer supply line 142 on the high pressure side of main pump 138 through a tee fitting 188'. Circulation pump 190 is coupled to return line 184' and, when activated, draws wash fluid from recirculation line 140 through main pump 138 and tee fitting 188' into return line 184', and conveys the wash fluid back to tank 102 through inlet 186. In addition, heated wash fluid from tank 102 is drawn into recirculation line 140 and through filter 136 (which is upstream of return line 184').

In addition, a solenoid valve 196 (also designated as S5) is coupled between sprayer supply line 142 and return line 184'. In operation, when main pump 138 is active during a washing action, solenoid valve 196 is closed while solenoid valve 156 is open such that pressurized wash fluid is directed from main pump 138 and through spray supply line 142 to sprayer 38. Conversely, when main pump 138 is idle and circulation pump 190 is activated, solenoid valve 196 is open while solenoid valve 156 is closed to circulate heated wash fluid through recirculation line 140, return line 184' and tank 102. By coupling return line 184' to the high pressure side of main pump 138, the thermal mass of main pump 138 (which can be considerable) is incorporated into the circulation path of the heated wash fluid, thereby promoting greater temperature stability throughout the recirculation system.

Figure 6B:
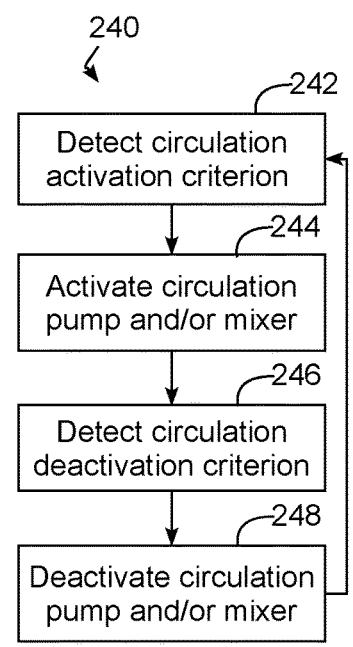
FIG. 6B is a flowchart illustrating an example sequence of operations for selectively activating a heated fluid circulation system in the beverage container washing system of FIG. 1.

Now turning to FIG. 6B, it may be desirable in some embodiments for a controller, e.g., controller 36 of beverage container washing system 10, to control heated wash fluid circulation system 182, e.g., by selectively activating circulation pump 190, to control the circulation of wash fluid retained in one or more lines between tank 102 and sprayer 38 back to tank 102. In some embodiments, for example, controller 36 may be configured to selectively activate circulation pump 190 while main pump 138 is idle, and to do so based upon one of several different types of activation criteria.

FIG. 6B, for example, illustrates a sequence of operations 240 for controlling circulation pump 190 and/or mixer 194, which begins in block 242 by detecting a circulation activation criteria, and in response to the detection, activating the circulation pump and/or mixer (block 244). Thereafter, a deactivation criterion may be detected (block 246) causing the pump and/or mixer to be deactivated (block 248).

In some embodiments, for example, the activation and deactivation criteria may be based upon whether the main pump is active. By doing so, the circulation pump may be active any time the main pump is idle. In some embodiments, the determination may be based specifically upon whether the main pump is currently active, while in other embodiments, the activation state of the main pump may be inferred from the state of the washing system, e.g., such that the circulation pump is shut off whenever a washing cycle is being performed, or whenever a washing cycle is determined to be in a phase during which the main pump is not active.

In other embodiments, the activation and/or deactivation criteria may be based upon whether the main pump has not been active for a predetermined time period. Thus, for example, if the washing system is being used on a regular basis, with relatively short durations between each washing cycle, the mixer and/or circulation pump may remain deactivated, while if the washing system has not been used for a sufficient period of time that allows the wash fluid temperature in the recirculation line to drop below a desirable level, the heated wash fluid circulation system may be activated.

In other embodiments, the activation and/or deactivation criteria may be based upon a sensed temperature, e.g., by temperature sensor 192, such that the heated wash fluid circulation system may be activated when the temperature has dropped below a predetermined setpoint and deactivated once the temperature returns to a suitable level.

In still other embodiments, the activation and/or deactivation criteria may be based upon a periodic activation cycle for the heated wash fluid circulation system, e.g., such that the circulation pump and/or mixer run at predetermined intervals and/or for predetermined durations.

Further, in some embodiments, multiple criteria may be used together, e.g., so that the heated wash fluid circulation system is run at periodic intervals, but only when the main pump is idle. Other variations will be appreciated by those of ordinary skill having the benefit of the instant disclosure, and therefore the invention is not limited to the specific criteria discussed herein.

Concentric Housing Members

As noted above, in some embodiments, it may be desirable to utilize a washing system design that incorporates a pair of concentric housing members that are supported on a base, with an inner one of the concentric housing members being disposed inwardly from the outer one of the concentric housing members and forming at least a portion of a wash chamber, and with each of the concentric housing members including an opening. Beverage container washing system 10 of FIGS. 1-2 illustrates such a concentric housing member arrangement, where concentric housing member 62 and outer concentric housing member 64 are configured as concentric domes that are generally dome shaped and have generally cylindrical sidewalls. It will be appreciated, however, that the concentric housing members can have a wide variety of alternate shapes, sizes and configurations, so the invention is not limited to the concentric dome configuration illustrated herein. As one example, in one embodiment an inner concentric housing member may have an open-top, e.g., configured as a cylinder, such that the top of the wash chamber is defined at least in part by the outer concentric housing member. By doing so, drying, spraying and/or ultraviolet sanitization actions may be performed at least in part by stationary components operating from an overhead position and not requiring electrical or other connections to a movable concentric housing member.

Figure 7:
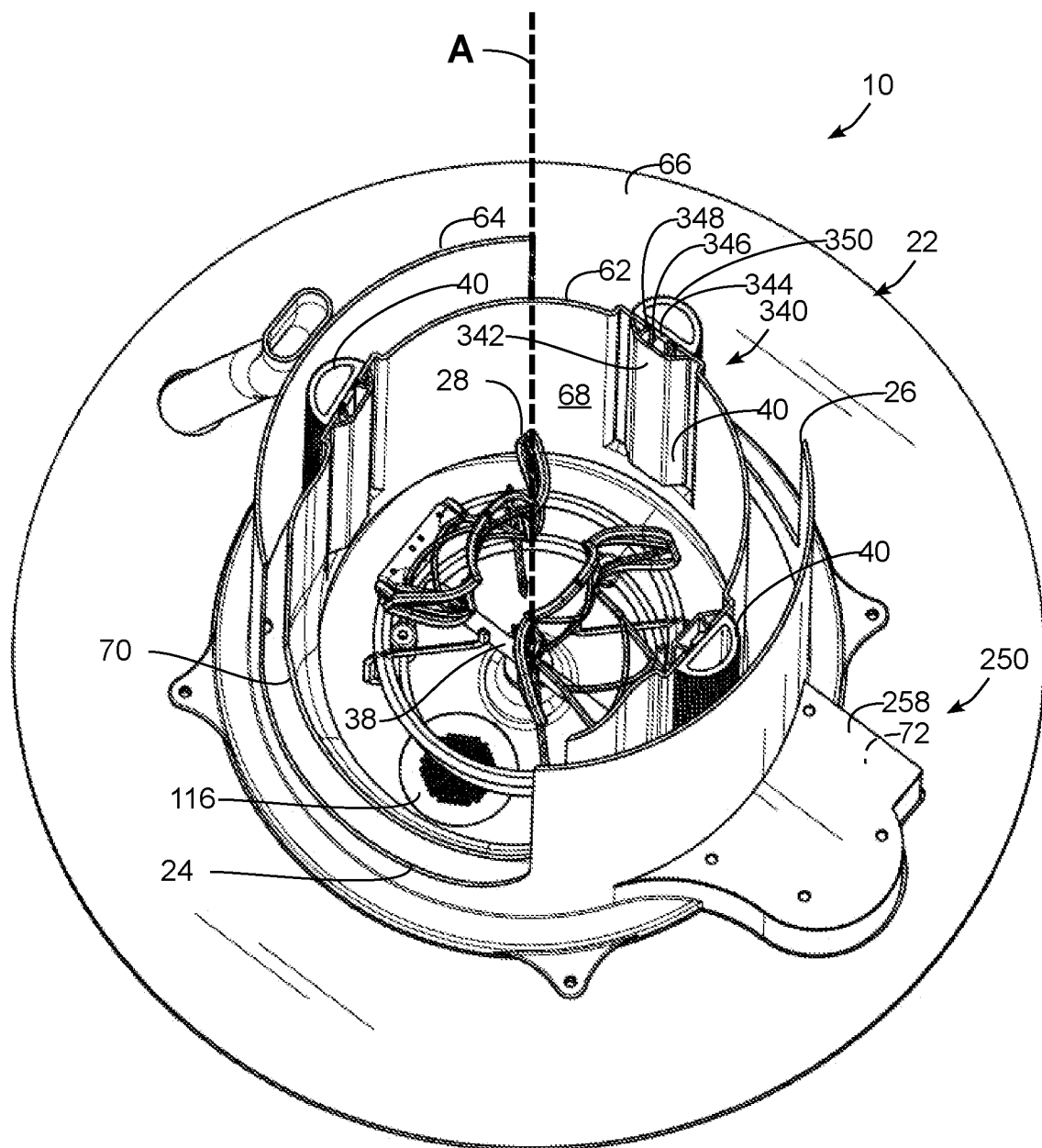
FIGS. 7-9 are cross-sectional views taken through the countertop portion of the beverage container washing system of FIG. 1 in respective loading, washing and unloading configurations.
Figure 8:
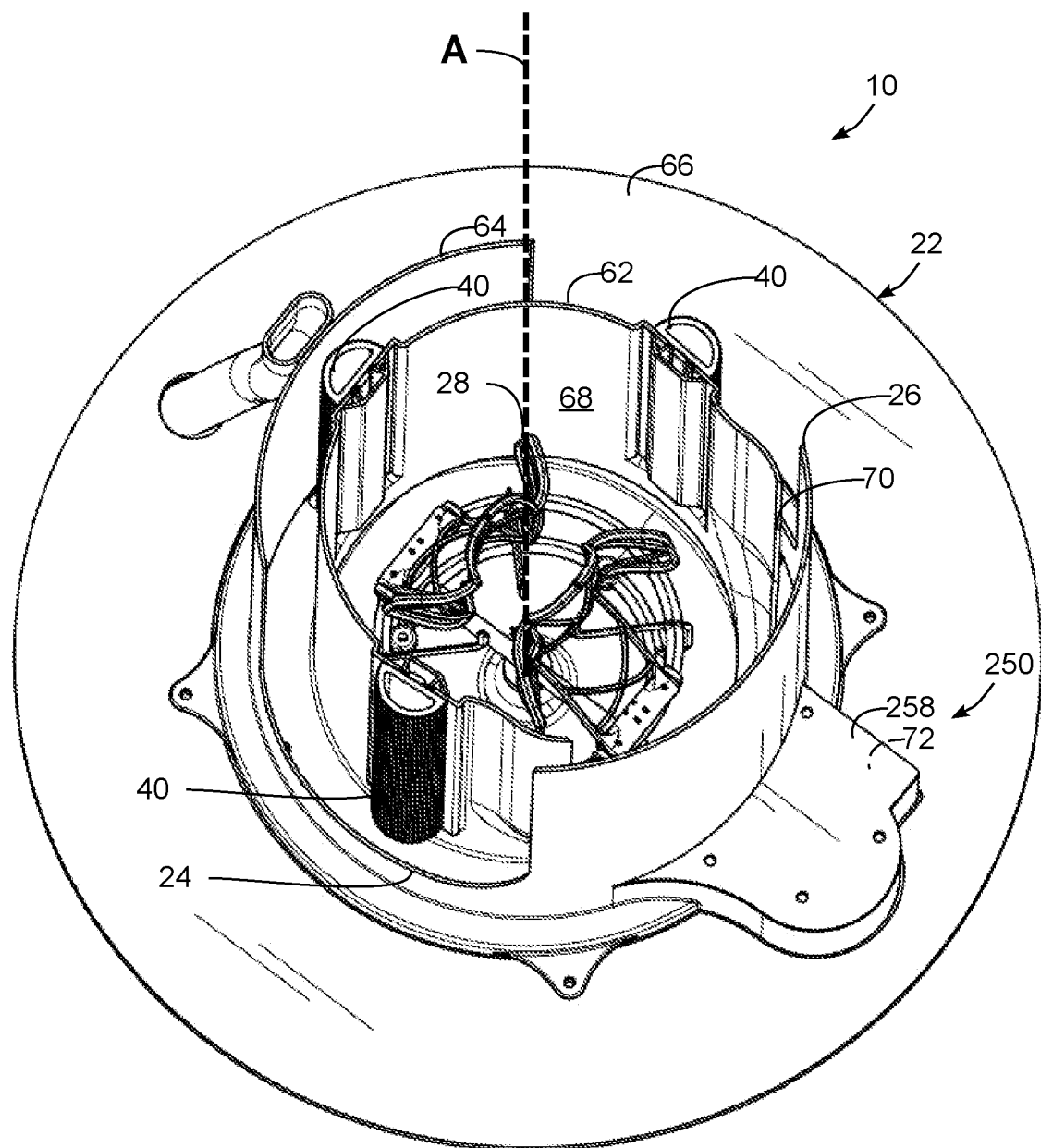
Figure 9:
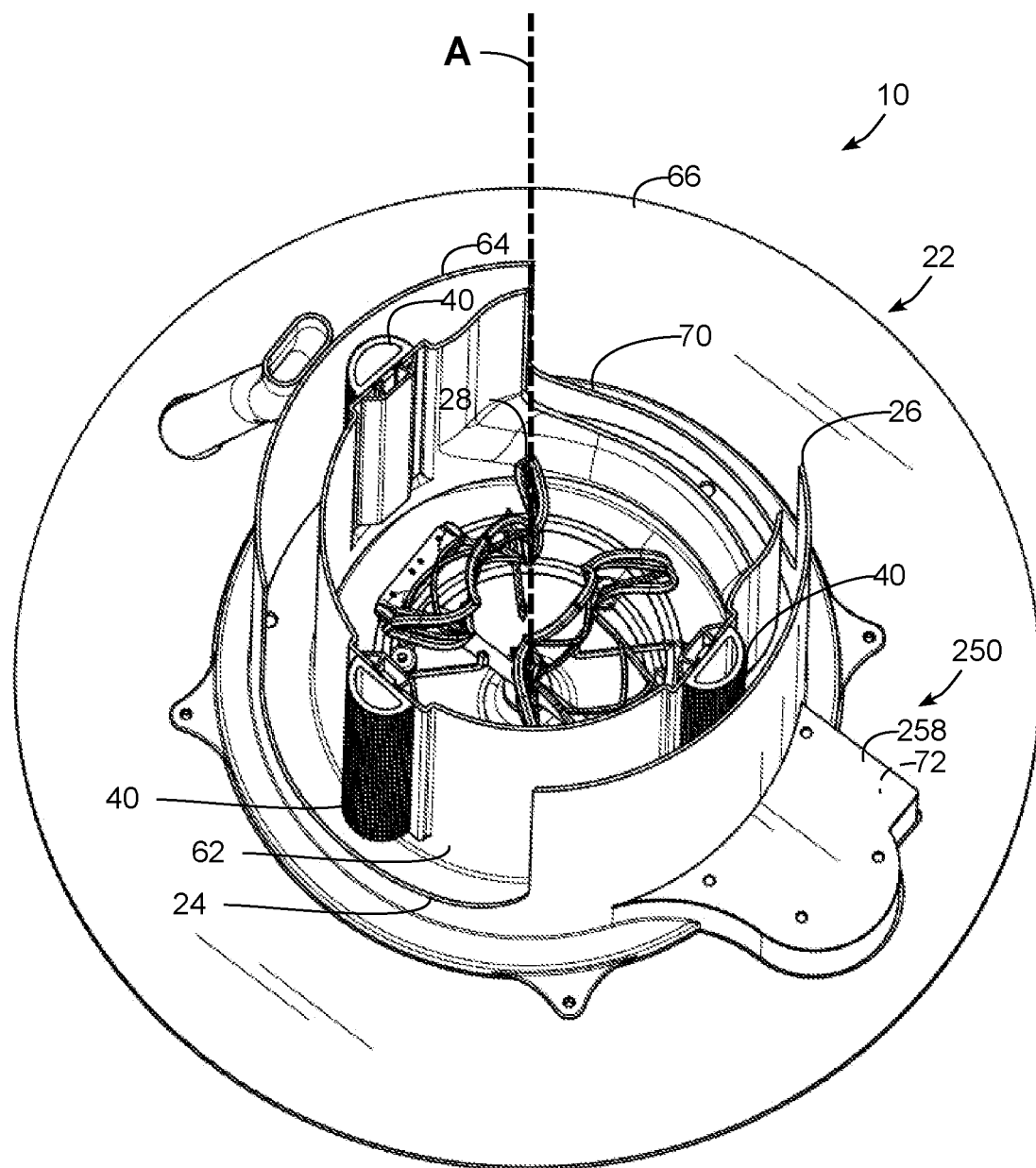

With further reference to FIGS. 7-9, each concentric housing member 62, 64 fully circumscribes an axis of rotation A, and among the concentric housing members 62, 64, inner concentric housing member 62 is rotatable while outer concentric housing member 64 is fixed or stationary. An entrance opening 24 and exit opening 26 are defined on opposite sides of outer concentric housing member 62 while an additional opening 70 is provided in inner concentric housing member 64, and a drive motor 72 is used to rotate inner concentric housing member 64 to selectively move opening 70 between a loading position where opening 70 is aligned with entrance opening 24 to provide access to the wash chamber for insertion of the beverage container prior to a washing operation (FIG. 7), a washing position where opening 70 is intermediate entrance and exit openings 24, 26 (thereby effectively closing both openings as shown in FIG. 8), and an unloading position where opening 70 is aligned with exit opening 26 to provide access to the wash chamber for removal of the beverage container at the completion of a washing operation (FIG. 9). The loading, washing and unloading positions represent different relative positions between the two concentric housing members 62, 64.

It will be appreciated that in some embodiments, the mere alignment or misalignment of opening 70 and entrance and exit openings 24, 26 may be sufficient to inhibit the escape of wash fluid from wash chamber 68. It should also be noted that opening 70 as illustrated in the figures does project radially from the inner cylindrical wall defining the wash chamber such that an edge of opening 70 may touch or at least define a reduced gap between opening 70 and the inner cylindrical wall of outer concentric housing member 64. In other embodiments, however, it may be desirable to also include a sealing arrangement on one or both of concentric housing members 62, 64 (e.g., around one or more of openings 24, 26 and 70) to further inhibit the escape of wash fluid from wash chamber 68.

Figure 10:
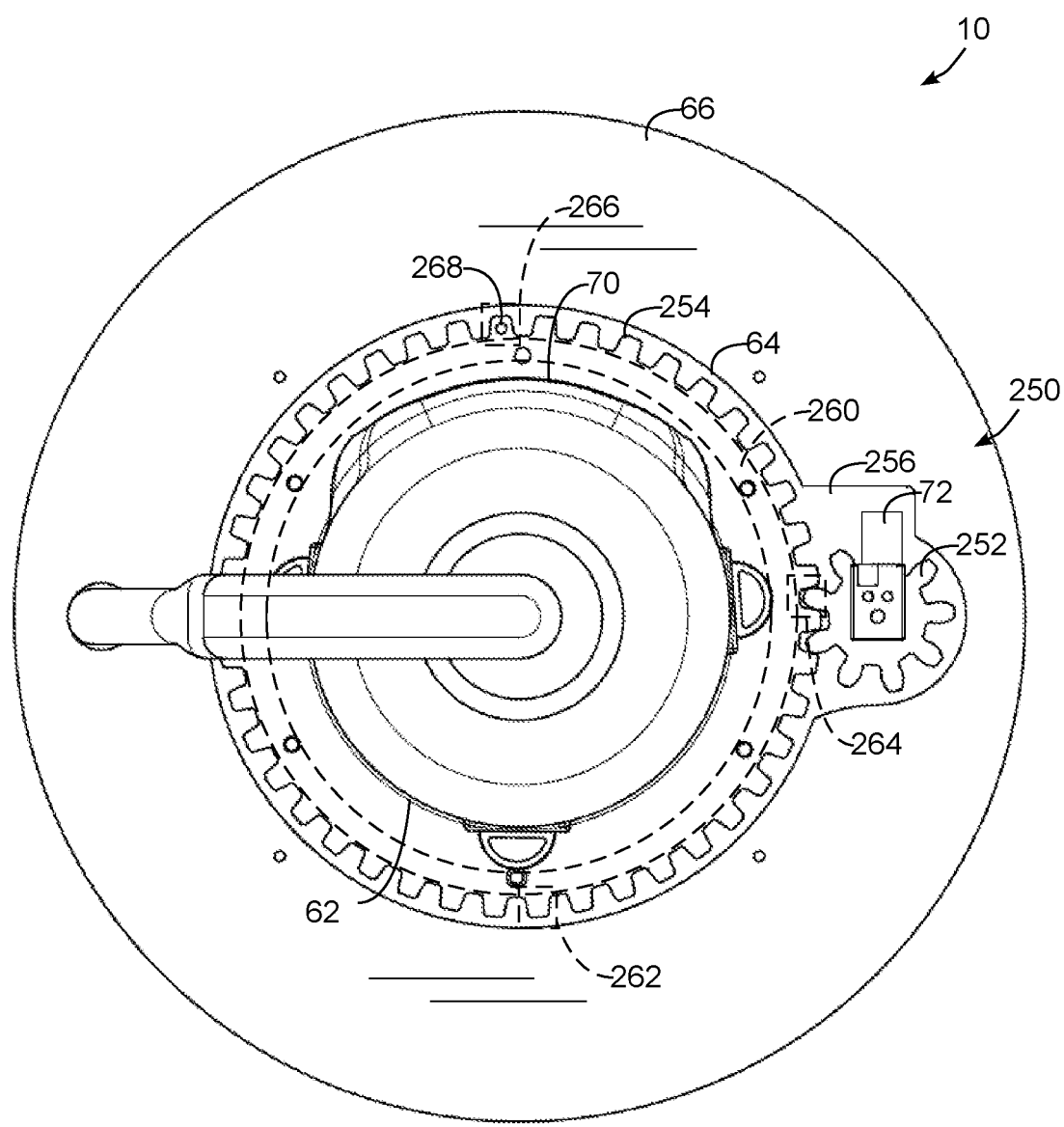
FIG. 10 is a partial top plan view of the beverage container washing system of FIG. 1, with portions thereof removed to illustrate a housing drive system thereof.

With additional reference to FIG. 10, drive motor 72 may be incorporated into a drive assembly 250 that further includes a pair of gears 252, 254 configured to drive rotation of inner concentric housing member 62 with drive motor 72. Drive motor 72 may be an electric, e.g. a DC motor, and drive motor 72 and gear 252 may be disposed in a compartment 256 formed in outer concentric housing member 64, and may be accessed through a cover 258. Gear 254 may be coupled to inner concentric housing member 62, and in some embodiments, may circumscribe the perimeter of the inner concentric housing member. In some embodiments, gear 254 may also be formed integrally with inner concentric housing member 62. In another embodiment, gear 254 may be formed as an internal ring gear and may be driven from a point inward from inner concentric housing member 62. Inner concentric housing member 62 may be rotatably supported on a turntable bearing 260. In other embodiments, other drive assembly configurations may be used to drive rotation of inner concentric housing member 62, e.g., a friction wheel drive assembly, a belt or chain drive, a piston or linear motor drive, etc. Particularly where rotation is limited to only about 90 degrees, as may be the case when two openings are provided in inner concentric housing member 62, various mechanical arrangements, including linear drives, may be used to impart sufficient rotation to the inner concentric housing member.

Furthermore, in order to controllably rotate inner concentric housing member 62 between the different relative positions, a position detector, e.g., an encoder or other suitable position sensor, may be used. In one embodiment, for example, a position detector may be implemented by a set of stationary three reed switches 262, 264, 266 configured to sense a magnet 268 coupled to inner concentric housing member 62 when the opening 70 is in each of the loading, washing and unloading positions. Other position detector configurations may be used in other embodiments, however, so it will be appreciated that the invention is not limited to the particular configuration illustrated in FIG. 10.

Dryer Assembly

As noted above in connection with FIGS. 1-2, it may also be desirable in some embodiments to incorporate a dryer assembly in a beverage container washing system, e.g., to blow off any standing wash fluid, water or other moisture left on the beverage container subsequent to spraying by a spraying assembly. It will be appreciated, however, that where the housing of the beverage container washing system incorporates movable components, supplying a flow air to the beverage container can be complicated by the need to supply the air in a manner that accommodates the movable components.

In the specific case of beverage container washing system 10, which incorporates a rotatable inner concentric housing member 62, for example, it is generally desirable to provide a flow of air to wash chamber 68, but do so in a manner that accommodates the rotatable nature of inner concentric housing member 62.

Figure 11:
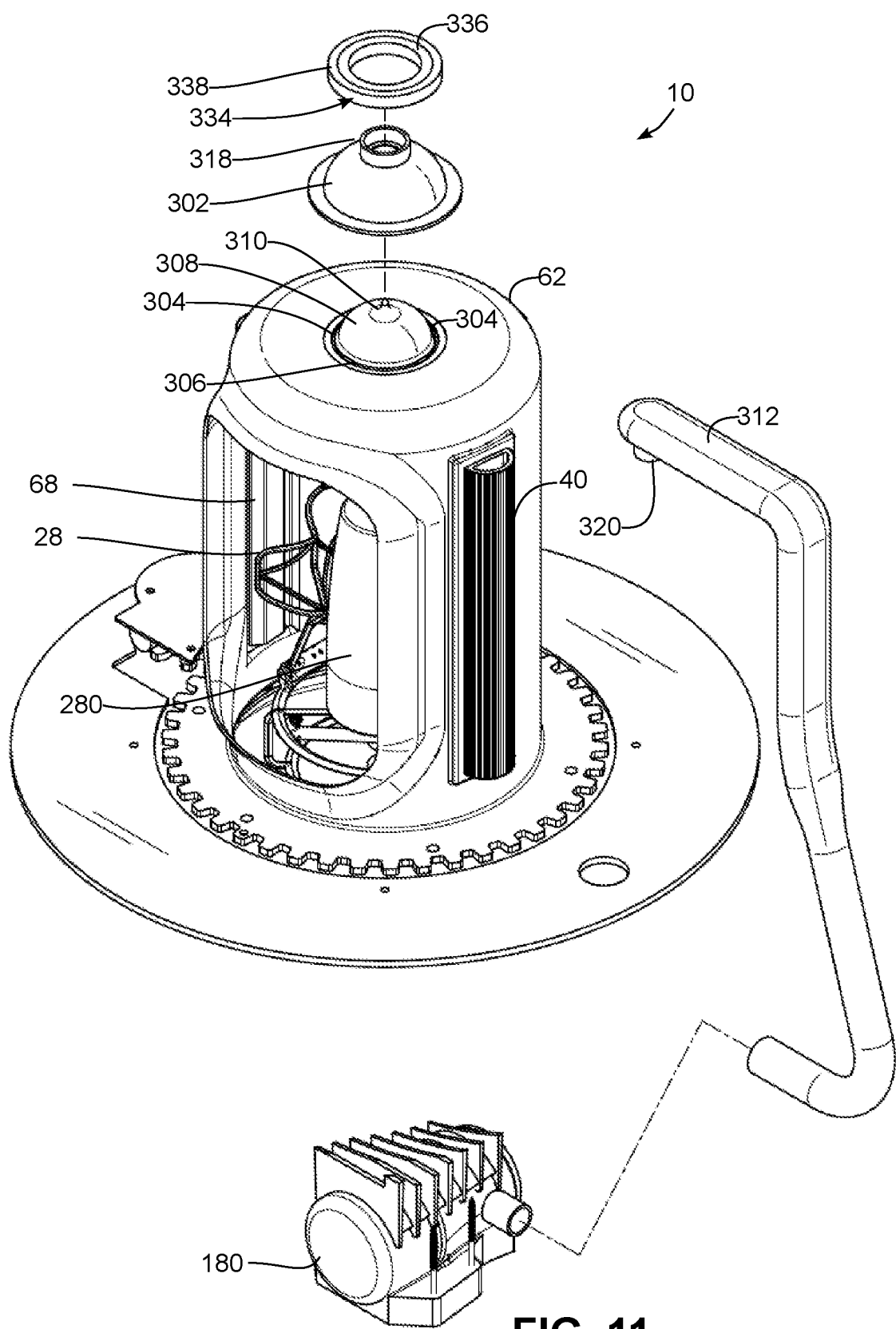
FIG. 11 is an exploded top perspective view of dryer assembly and ultraviolet sanitizing assembly components of the beverage container washing system of FIG. 1.
Figure 12:
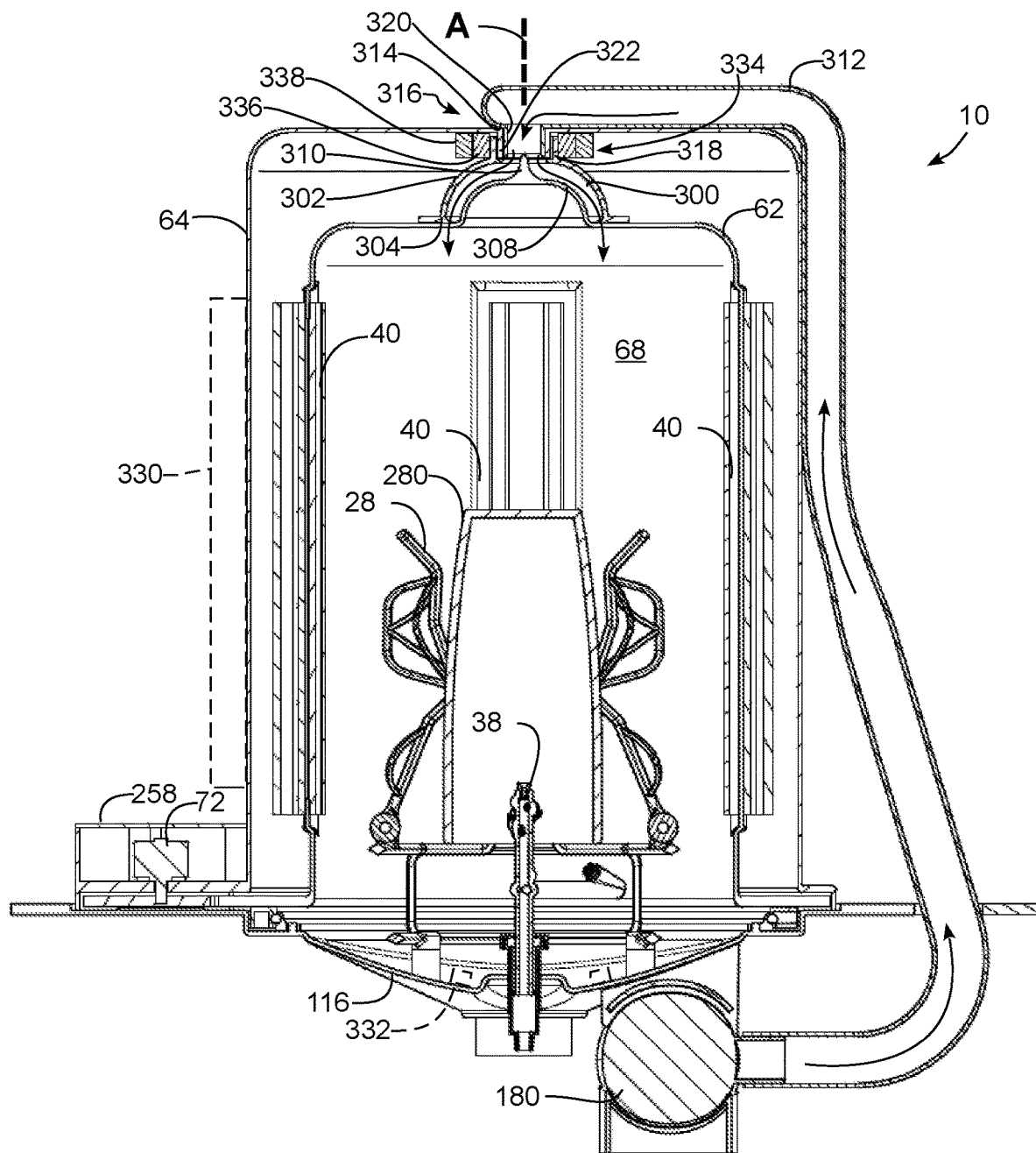
FIG. 12 is a side cross-sectional view of dryer assembly and ultraviolet sanitizing assembly components of the beverage container washing system of FIG. 1.

In the illustrated embodiment, and with further reference to FIGS. 11-12 (note that outer concentric housing member 64 has been omitted from FIG. 11), a dryer assembly may include an air knife chamber 300 disposed proximate a top of inner concentric housing member 62. Air knife chamber 300 is defined in part by an outer shell 302, which, in some embodiments, may be integrally molded or formed with inner concentric housing member 62, while in other embodiments, may be welded, fastened, or otherwise secured to a wall of inner concentric housing member 62 such that the outer shell 302 covers at least a portion of the wall of the inner concentric housing member. In the illustrated embodiment, outer shell 302 and air knife chamber 300 are configured to rotate with the inner concentric housing member, while in other embodiments, outer shell 302 and air knife chamber 300 may be stationary, such that inner concentric housing member 62 rotates relative to the outer shell and the air knife chamber.

One or more air knife openings 304 are defined in inner concentric housing member and are in fluid communication with air knife chamber 300 to direct a flow of air toward a beverage container 280 while the beverage container is held by holder 28 in wash chamber 68. In the illustrated embodiment, for example, an annular arrangement of four radially-offset and arcuate air knife openings 304 (which at least partially circumscribe the axis of rotation A) are used, which are separated from one another by four tabs 306 that support a central hub 308 having a central nipple 310. As seen in FIG. 12, the shape of central hub 308 and central nipple 310 serves to distribute air flow radially outwardly to the air knife openings 304 that are radially-offset from the axis of rotation A. Moreover, in the illustrated embodiment, central nipple is upwardly-facing and axially aligned with the axis of rotation A.

Air is suppled to air knife chamber 300 from a stationary air supply conduit 312 that is in fluid communication with blower 180 to receive a supply of pressurized air. In the illustrated embodiment, at least a portion of conduit 312 extends substantially vertically along a side of outer concentric housing member 64, around a top side of outer concentric housing member 64, and then through an opening 314 formed in the top side of outer concentric housing member 64.

Air knife chamber 300 is in fluid communication with stationary air supply conduit 312 through a rotary seal 316, which in the illustrated embodiment is formed by a three concentric tubes 318, 320, 322 that are all axially aligned with the axis of rotation A. Concentric tube 318 is an upwardly-facing tube that defines an air inlet for air knife chamber 300, while concentric tube 320 is a downwardly-facing tube that extends downwardly from stationary air supply conduit 312 and forms an air outlet therefor. Concentric tube 322 is also downwardly-facing, but extends downwardly from outer concentric housing member 64 and defines opening 314. In the illustrated embodiment, concentric tube 322 is inward of concentric tube 318, and concentric tube 320 is inward of concentric tube 322, with at least portions of all three concentric tubes overlapping with one another to form the rotary seal. Moreover, in some embodiments, rotary seal 316 also functions as an axle for rotation of inner concentric housing member 62 to rotate about axis of rotation A. As such, air from stationary air supply conduit 312 may be provided to wash chamber 68 through rotating concentric housing member 62.

It will be appreciated that other rotary seals may be used in other embodiments, so the invention is not limited to the concentric tube arrangement illustrated in FIGS. 11-12. Moreover, it will be appreciated that a wide variety of alternate numbers and configurations of air knife openings may be used in other embodiments, e.g., to direct air in multiple directions and at other regions of a beverage container, including, in some embodiments, an interior of the beverage container. Additional stationary air knife openings may also be used in some embodiments, e.g., directed upwardly from base 66, and in some embodiments, no movable air knives may be used, or drying may not be supported whatsoever in a cup washing system. Where an inner concentric housing member has an open top, as another example, stationary air knives may be used in lieu of the configuration illustrated in FIGS. 11-12. Further, air knife openings may be configured in other manners in other embodiments, e.g., using nozzles capable of controlling direction, flow rate and/or spray pattern, as will be appreciated by those of ordinary skill in the art having the benefit of the instant disclosure.

Ultraviolet Sanitizing Assembly

As also noted above in connection with FIGS. 1-2, it may also be desirable in some embodiments to incorporate an ultraviolet sanitizing assembly in a beverage container washing system, e.g., to sanitize an outer and/or inner surface of a beverage container by irradiating it with ultraviolet light. It will be appreciated, however, that where the housing of the beverage container washing system incorporates movable components, supplying power to ultraviolet lights mounted to such movable components can be complicated by the need to supply the power in a manner that accommodates the movable components. In the specific case of beverage container washing system 10, which incorporates a rotatable inner concentric housing member 62, for example, it may be desirable to provide one or more ultraviolet lights 40 within wash chamber 68, but do so in a manner that accommodates the rotatable nature of inner concentric housing member 62.

Ultraviolet sanitizing lights, which are generally formed by arrays of ultraviolet (UV) light emitting diodes (LEDs), or alternatively by other devices capable of emitting ultraviolet light (e.g., incandescent or halogen lights), are susceptible to being attenuated by materials lacking sufficient transmissivity to ultraviolet wavelengths, and in some instances, UV LEDs may require special materials that offer a unique transmissivity, as the UV light may be attenuated even by some visually translucent materials. As such, it may be desirable in some embodiments to avoid the high cost of creating large parts that are UV light transmissive by restricting the amount of material between the UV LEDs and the beverage container to be sanitized. In the illustrated embodiment, therefore, incorporating UV LEDs into the inner concentric housing member 62 may reduce potential transmissivity issues, and may even allow for the inner concentric housing member 62 to be formed from a material that is translucent or transparent to visible light but that is more opaque to ultraviolet light. Various materials that may be used in some embodiments are polycarbonate, acrylic, standard Glass, etc., although other materials may be used. In some instances, this may even provide a pleasing visual effect for users, as the visual light emitted by the UV LEDs may be visible through the inner (and outer, if formed of a similar material) concentric housing member 62, while still blocking user exposure to ultraviolet wavelengths.

In the illustrated embodiment, and with continuing reference to FIGS. 11-12 (note that outer concentric housing member 64 has been omitted from FIG. 11), an ultraviolet sanitizing assembly may include one or more ultraviolet lights 40 that are coupled to a rotatable concentric housing member, in this case inner concentric housing member 62. As noted above, while ultraviolet lights 40 may be implemented using one or more UV LEDs, in other embodiments, other devices capable of emitting ultraviolet light (e.g., incandescent or halogen lights) may also be used. In other embodiments, e.g., where an outer concentric housing member is rotatable, one or more ultraviolet lights may be mounted to an outer concentric housing member. Further, in some embodiments, additional ultraviolet lights may be located in fixed or stationary locations, e.g., as illustrated in FIG. 12 by ultraviolet light 330 on outer concentric housing member 64, as illustrated in FIG. 12 by ultraviolet light 332 in collector 116, or in other locations such as the space between concentric housing members 62, 64.

It should be noted that in some embodiments ultraviolet light 330 may be positioned on outer concentric housing member 64 such that opening 70 of inner concentric housing member 62 faces ultraviolet light 330 when in the washing position, such that three ultraviolet lights 40 may be disposed on inner concentric housing member 62, and with all four ultraviolet lights 40, 330 evenly spaced in 90 degree increments about the axis of rotation to provide relatively full coverage of the outer surface of beverage container 280. It should also be noted that some ultraviolet lights, e.g., ultraviolet light 332, may be positioned to irradiate an inner surface of beverage container 280.

In order to power ultraviolet lights 40, a slip ring 334 may be coupled between inner and outer concentric housing members 62, 64, with, for example, a rotatable portion 336 coupled to inner concentric housing member 62 and a stationary portion coupled to outer concentric housing member 64. Slip ring 334 may utilize various electromechanical constructions, including rotary electrical contacts, commutators, rotary transformers, rotary unions, pancake slip rings, wireless slip rings, etc., and wiring harnesses (not shown) both on the stationary and rotatable sides of the slip ring may be used to route the electrical power to each ultraviolet light 40. Further, slip ring 334 may be positioned elsewhere within housing 22, e.g., along the top or side wall of inner concentric housing member 62, at the base of inner concentric housing member 62, etc.

Various ultraviolet light constructions may be used for ultraviolet lights 40 in different embodiments. In the illustrated embodiment, for example, each ultraviolet light 40 may extend substantially vertically along a side wall of inner concentric housing member 62, and in some instances, and as best illustrated in FIGS. 7-9, the inner concentric housing member 62 may include a substantially vertical mounting arrangement 340 configured to receive each ultraviolet light 40.

The mounting arrangement 340 in some embodiments may include an ultraviolet transmissive cover 342 that overlays ultraviolet light 40 to permit ultraviolet light transmission into wash chamber 68, and that further seals the ultraviolet light from the wash chamber. In some instances, the cover 342 may be mounted, welded or otherwise secured to inner concentric housing member 62, while in other instances, the cover may be integrally molded thereto. In either instance, it is generally desirable for the other walls of inner concentric housing member 62 to be formed of an ultraviolet blocking material that inhibits ultraviolet light transmission through the walls of inner concentric housing member 62.

The mounting arrangement may 340 may also include one or more openings 344 formed in a wall of inner concentric housing member 62 and aligned with a plurality of UV LEDs 346 disposed on a circuit board 348. By doing so, circuit board 348 may be positioned on an outer surface of inner concentric housing member 62, with the UV LEDs 346 positioned to emit ultraviolet light through openings 344. In addition, in some embodiments, it may also be desirable to incorporate a heat sink 350, which may run along a portion or the entire length of circuit board 348 and be thermally coupled thereto, and serve to further seal the circuit board from the surrounding environment.

It will be appreciated that different numbers and/or orientations of ultraviolet lights may be used in other embodiments, e.g., two ultraviolet lights having respective angular positions about the axis of rotation A spaced about 90 to about 180 degrees, or less, from one another, three ultraviolet lights having respective angular positions about the axis of rotation A spaced about 90 to about 120 degrees from one another, four ultraviolet lights having respective angular positions about the axis of rotation A spaced about 90 degrees or less from one another, etc. In one example embodiment, for example, two opposing ultraviolet lights may be supported on inner concentric housing member 62 and two opposing ultraviolet lights may be supported on outer concentric housing member 64 such that ultraviolet lights are oriented in 90 degree increments when the inner concentric housing member 62 is in the washing position.

Figure 13:
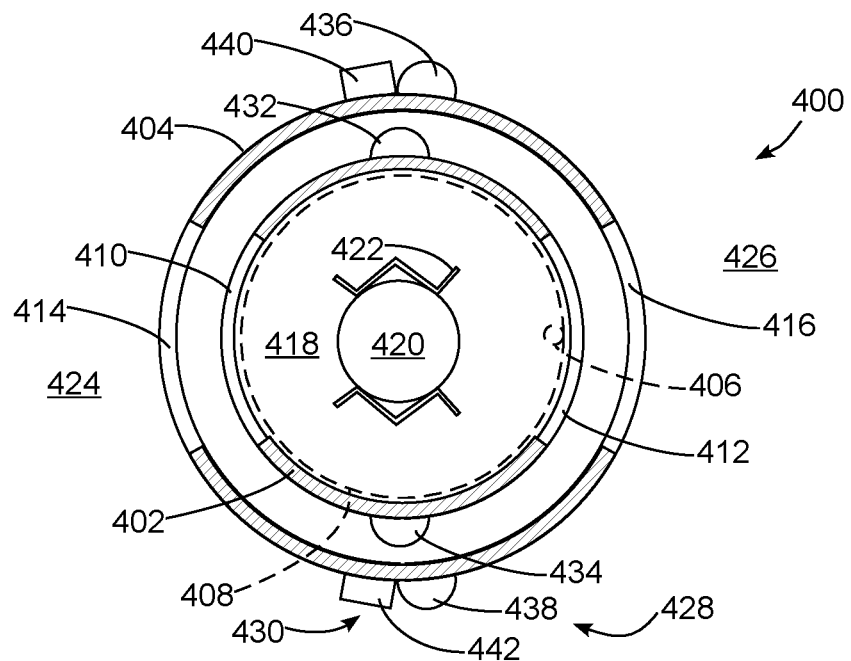
FIGS. 13 and 14 are functional top plan views of another beverage container washing system consistent with some embodiments of the invention.
Figure 14:
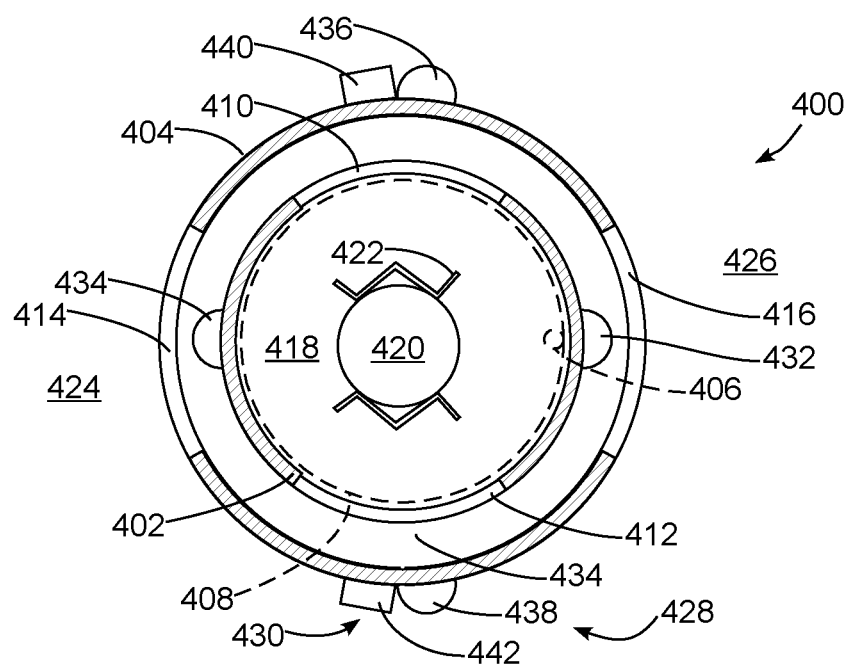

Beverage Container Washing System with Multiple Openings and Through Opening Air Knives Next, with reference to FIGS. 13 and 14, another beverage container washing system 400 consistent with the invention includes an inner concentric housing member 402 and an outer concentric housing member 404 configured as concentric domes that are generally dome shaped and have generally cylindrical sidewalls, with inner concentric housing member 402 being rotatable and driven by a drive motor (not shown) coupled to a gear 406 that drives a ring gear 408 attached to inner concentric housing member 402. Outer concentric housing member 404 is fixed or stationary. In this embodiment, inner concentric housing member 402 includes multiple openings, e.g., first and second openings 410, 412, while outer concentric housing member 404 includes first and second openings 414, 416 (e.g., entrance and exit openings, respectively), with each pair of openings disposed on substantially opposite sides from one another (e.g., about 180 degrees angularly offset from one another).

When inner concentric housing member 402 is rotated to the orientation illustrated in FIG. 13, it will be appreciated that openings 410 and 414 are aligned, as are openings 412, 416. By doing so, access to a wash chamber 418 is provided, enabling for insertion and/or removal of a beverage container 420 into and/or out of a holder 422 through either aligned openings 410, 414 on side 424 of beverage container washing system 400 or aligned openings 412, 416 on side 426 of washing system 400. A rotation of inner concentric housing member 404 of about a quarter turn (about 90 degrees) in either direction results in the configuration illustrated in FIG. 14, where it may be seen that openings 410, 412 of inner concentric housing member 402 are now facing the sidewall of outer concentric housing member 404, and are unaligned with openings 414, 416. By doing so, wash chamber 418 is effectively closed off for a washing operation, and the sidewall of inner concentric housing member 402 minimizes the escape of wash fluid through openings 414, 416.

In this configuration, the orientation illustrated in FIG. 13 may be considered to function both as a loading position and an unloading position, with the orientation illustrated in FIG. 14 functioning as a washing position. Furthermore, it will be appreciated that an orientation where inner concentric housing member 402 is rotated 180 degrees relative to that illustrated in FIG. 13, where openings 410, 412 of inner concentric housing member 402 are aligned with openings 416, 414 of outer concentric housing member 404, respectively, may also be considered to represent loading and/or unloading positions. In addition, an orientation where inner concentric housing member 402 is rotated 180 degrees relative to that illustrated in FIG. 14 may also be considered to be a washing position. Moreover, transitioning between loading, washing and unloading positions may occur in different manners in different embodiments. In one embodiment, for example, a 90 degree rotation in one direction may transition from a loading position to a washing position, followed by another 90 degree rotation in the same direction to transition from the washing position to the unloading position. In another embodiment, a 90 degree rotation in one direction may transition from a loading position to a washing position, followed by a 90 degree rotation in the opposite direction to transition from the washing position to the unloading position. Further, it will be appreciated that with the use of two openings in the inner concentric housing member, no transition may be required between the unloading and loading positions at the completion of a washing operation, since the same relative positions may be used for both unloading and loading (although in other embodiments, a 180 degree rotation may be used if desired to transition between unloading and loading positions). Thus, while reference is made herein to separate loading and unloading positions, it will be appreciated that such positions may be represented by the same relative positions between the inner and outer concentric housing members 402, 404 in some embodiments.

Beverage container washing system 400 also illustrates an alternative ultraviolet sanitizing assembly 428 and dryer assembly 430 that may be suitable for use in some embodiments. Ultraviolet sanitizing assembly 428 in this embodiment includes a first pair of ultraviolet lights 432, 434 that are mounted to inner concentric housing member 402 in a similar manner to ultraviolet lights 40 as described above, with each positioned on opposite sides intermediate openings 410, 412, as well as a second pair of ultraviolet lights 436, 438 that are mounted to outer concentric housing member 404 and positioned on opposite sides intermediate openings 414, 416. In this configuration, and as seen in FIG. 14, when in a washing position, ultraviolet lights 432, 434, 436 and 438 are relatively evenly spaced about the periphery of wash chamber 418, thus providing substantially 360 degree exposure to the outside of beverage container 420. Moreover, ultraviolet lights 436 and 438 are respectively aligned with openings 410, 412 of inner concentric housing member 402 such that the sidewall of inner concentric housing member 402 does not block the ultraviolet radiation emitted by ultraviolet lights 436, 438.

Dryer assembly 430 in this embodiment includes a pair of stationary through opening air knives 440, 442 that are supplied by a blower and, as illustrated in FIG. 14, are aligned with openings 410, 412 of inner concentric housing member 402 such that the sidewall of inner concentric housing member 402 does not block airflow from the through opening air knives 440, 442. It will be appreciated that in some embodiments, through opening air knives 440, 442 may be used instead of the top-down configuration illustrated in FIGS. 11-12, while in other embodiments, through opening air knives 440, 442 may be used in addition to the aforementioned top-down configuration of FIGS. 11-12.

Next, with reference to FIGS. 15-18, and initially with specific reference to FIG. 15, another beverage container washing system 500 consistent with the invention is illustrated, having a similar construction to beverage container washing system 400 of FIGS. 13-14, but also including integrated ultraviolet light and through opening air knife assemblies. System 500, in particular, includes an inner concentric housing member 502 and an outer concentric housing member 504 configured as concentric domes that are generally dome shaped and have generally cylindrical sidewalls, with inner concentric housing member 502 being rotatable and driven by a drive motor (not shown) coupled to a gear 506 that drives a ring gear 508 attached to inner concentric housing member 502. Outer concentric housing member 504 is fixed or stationary. In this embodiment, inner concentric housing member 502 includes multiple openings, e.g., first and second openings 510, 512, while outer concentric housing member 504 includes first and second openings 514, 516 (e.g., entrance and exit openings, respectively), with each pair of openings disposed on substantially opposite sides from one another (e.g., about 180 degrees angularly offset from one another).

Similar to inner concentric housing member 402 of system 400, inner concentric housing member 502 is rotatable between an orientation or position (also referred to as a loading and/or unloading position, similar to that illustrated in FIG. 13) in which openings 510, 512 are respectively aligned with openings 514, 516 (thereby providing external access to a wash chamber 518) and another orientation or position (also referred to herein as a washing position and illustrated in FIG. 15) in which openings 510, 512 are not aligned with openings 514, 516 (thereby restricting external access to wash chamber 518). Specifically, the former position enables insertion and/or removal of a beverage container 520 into and/or out of a holder 522 through either aligned openings 510, 514 on side 524 of beverage container washing system 500 or aligned openings 512, 516 on side 526 of washing system 500. A rotation of inner concentric housing member 504 of about a quarter turn (about 90 degrees) in either direction results in the configuration illustrated in FIG. 15, where it may be seen that openings 510, 512 of inner concentric housing member 502 are now facing the sidewall of outer concentric housing member 504, and are unaligned with openings 514, 516. By doing so, wash chamber 518 is effectively closed off for a washing operation, and the sidewall of inner concentric housing member 502 minimizes the escape of wash fluid through openings 514, 516.

Beverage container washing system 500 also illustrates a pair of integrated ultraviolet light and through opening air knife assemblies 528, 530 that may be suitable for use in some embodiments. Integrated ultraviolet light and through opening air knife assembly 528 includes an ultraviolet light 532 and a through opening air knife 534, while integrated ultraviolet light and through opening air knife assembly 530 includes an ultraviolet light 536 and a through opening air knife 538, and it will be appreciate that in the illustrated embodiment of FIG. 15, ultraviolet lights 532, 536 are about 180 degrees offset from one another about the axis of rotation A, as are through opening air knives 534, 538. Furthermore, a pair of additional ultraviolet lights 540, 542 may also be mounted to inner concentric housing member 502 in a similar manner to ultraviolet lights 432, 434 of beverage container washing system 400, with each positioned on opposite sides intermediate openings 510, 512. In this configuration, and as seen in FIG. 15, when in a washing position, ultraviolet lights 532, 536, 540 and 542 are relatively evenly spaced about the periphery of wash chamber 518, thus providing substantially 360 degree exposure to the outside of beverage container 520. Moreover, ultraviolet lights 532 and 536 are respectively aligned with openings 510, 512 of inner concentric housing member 502 such that the sidewall of inner concentric housing member 502 does not block the ultraviolet radiation emitted by ultraviolet lights 536, 538.

Through opening air knives 534, 538, as noted above, direct air flow through openings 510, 512 of inner concentric housing member 502 when inner concentric housing member 502 is in the washing position. In the illustrated embodiment of FIG. 15, through opening air knives 534, 538 are positioned and oriented to direct air flow over opposite sides of beverage container 520, as represented by lines 540, 542, which flow across opposing sides of beverage container 520 facing sides 524, 526 of beverage container washing system 500. In some embodiments, for example, and as illustrated in FIG. 15, each ultraviolet light 532, 536 may be configured to emit ultraviolet light directed along a respective radial 544, 546 extending from axis of rotation A, and each through opening air knife 534, 536 may be laterally offset from its associated ultraviolet light 532, 536 and configured to direct air flow along flow lines 540, 542 that are substantially parallel to radials 544, 546, and in some instances, such that the air flow wraps around the sides of the beverage container. Further, in some instances, the air flow may generate a vortex effect within the wash chamber to remove moisture from the surfaces of the beverage container.

FIGS. 16-18 illustrate integrated ultraviolet light and through opening air knife assembly 528 in greater detail. It will be appreciated that in some embodiments, integrated ultraviolet light and through opening air knife assembly 530 may be similarly configured. A housing 548 has a first end 550 and a second end 552, and when assembly 528 is substantially vertically oriented as illustrated in FIG. 15, first end 550 generally corresponds to the bottom of housing 548 and second end 552 generally corresponds to the top of housing 548.

Ultraviolet light 532 may include a plurality of UV LEDs 554 sealed by a UV-transmissive cover 556, e.g., formed of plastic, glass or silicone. In addition, in order to dissipate heat generated by UV LEDs 554, a heat sink 558 may be formed on a rear side of housing 548. As such, it may be desirable to construct housing 548 from a heat transmissive material such as various metals, e.g., via casting or machining. Alternatively, heat sink 558 may formed from a different material from housing 548 and fastened or otherwise mounted thereto.

For air knife 534, an inlet 560 may be in fluid communication with one or more outlets 562 through an internal air channel 564 such that pressurized fluid, e.g., air from an air supply, may be directed towards the beverage container. Inlet 560, in some implementations, may be disposed proximate first end 550, while outlet(s) 562 may be disposed on a sidewall 566 of housing 548.

In some embodiments, outlet(s) 562 may include a single elongated slot as illustrated in FIG. 16, and in order to balance air flow over the length of the slot, either the slot, air channel 564, or both, may narrow from the direction of first end 550 to the direction of second end 552 as illustrated in FIG. 16. In other embodiments, however, more than one outlet may be used. For example, as illustrated in phantom in FIG. 18, outlets may be formed in some instances as distinct nozzles 568, and in some instances, nozzles may be movable, e.g., oscillating or rotating, as illustrated at 570.

Moreover, as illustrated in FIG. 18, one or more outlets 562 may be configured to direct air flow in a substantially horizontal direction. Alternatively, as illustrated at 572 air flow may alternatively be directed in a slightly upward or slightly downward direction, and different outlets may direct air flow in different directions.

Various modifications may be made to the illustrated embodiments. For example, outer dome 504 may be rotatable and inner dome 502 may be stationary, or both domes may be rotatable. Furthermore, in other embodiments, air knives 534, 538 may be disposed in separate housings from ultraviolet lights 532, 536, and in some embodiments, air knives 534, 538 may be movable, e.g., with a dome and/or in a vertical and/or horizontal direction. In some embodiments, for example, air knives 534, 538 may oscillate to sweep air flow across different portions of a beverage container. Furthermore, different numbers of air knives and/or different numbers of dome openings may be used in other embodiments, and moreover, different mounting locations may be used for air knives in various embodiments, e.g., mounted to a dome, between domes, or supported in other manners that will be apparent to those of ordinary skill having the benefit of the instant disclosure.

It will be appreciated that, while certain features may be discussed herein in connection with certain embodiments and/or in connection with certain figures, unless expressly stated to the contrary, such features generally may be incorporated into any of the embodiments discussed and illustrated herein. Moreover, features that are disclosed as being combined in some embodiments may generally be implemented separately in other embodiments, and features that are disclosed as being implemented separately in some embodiments may be combined in other embodiments, so the fact that a particular feature is discussed in the context of one embodiment but not another should not be construed as an admission that those two embodiments are mutually exclusive of one another. Various additional modifications may be made to the illustrated embodiments consistent with the invention. Therefore, the invention lies in the claims hereinafter appended.

What is claimed is:

1. An apparatus for washing a beverage container, comprising:

first and second concentric housing members, each of the first and second concentric housing members including an opening, and one of the first and second concentric housing members being disposed inwardly from the other of the first and second concentric housing members and defining at least a portion of a wash chamber, wherein the first concentric housing member is rotatable about an axis of rotation between first and second positions, wherein when in the first position, the opening of the first concentric housing member is aligned with the opening of the second concentric housing member to provide external access to the wash chamber, and wherein when in the second position, the opening of the first concentric housing member is unaligned with the opening of the second concentric housing member to restrict external access to the wash chamber; and an air knife positioned to direct air flow through the opening of the one of the first and second concentric housing members that is disposed inwardly from the other of the first and second concentric housing members and into the wash chamber when the first concentric housing member is disposed in the second position.

2. The apparatus of claim 1, wherein the first concentric housing member is disposed inwardly from the second concentric housing member.

3. The apparatus of claim 2, wherein the second concentric housing member is stationary.

4. The apparatus of claim 3, wherein the air knife is mounted to the second concentric housing member.

5. The apparatus of claim 1, wherein the opening of the first concentric housing member is a first opening and the first concentric housing member includes a second opening, the opening of the second concentric housing member is a first opening and the second concentric housing member includes a second opening, and the second openings of the first and second concentric housing members are aligned with one another when the first concentric housing member is in the first position.

6. The apparatus of claim 5, wherein the air knife is a first air knife, the apparatus further comprising a second air knife positioned to direct air flow through the second opening of the one of the first and second concentric housing members that is disposed inwardly from the other of the first and second concentric housing members and into the wash chamber when the first concentric housing member is disposed in the second position.

7. The apparatus of claim 6, wherein the first and second openings of the first concentric housing member are 180 degrees offset from one another about the axis of rotation, the first and second openings of the second concentric housing member are 180 degrees offset from one another about the axis of rotation, and the first and second air knife are 180 degrees offset from one another about the axis of rotation.

8. The apparatus of claim 7, wherein the first air knife is oriented to direct air flow along a first side of the beverage container and the second air knife is oriented to direct air flow along a second side of the beverage container that is opposite the first side of the beverage container.

9. The apparatus of claim 1, wherein the air knife includes a housing and an air channel disposed within the housing, and the housing includes an inlet in fluid communication with the air channel and configured to receive pressurized fluid from an air supply and one or more outlets in fluid communication with the air channel and configured to direct the received pressurized fluid toward the beverage container.

10. The apparatus of claim 9, wherein the inlet is disposed proximate a first end of the housing, and the one or more outlets are disposed on a sidewall of the housing.

11. The apparatus of claim 10, wherein the air channel narrows from a direction of the first end of the housing to a direction of a second end of the housing to balance air flow proximate the second end of the housing with air flow proximate the first end of the housing.

12. The apparatus of claim 11, wherein each of the one or more outlets narrows from the direction of the first end of the housing to the direction of the second end of the housing to balance air flow exiting the one or more outlets.

13. The apparatus of claim 12, wherein the one or more outlets comprises a slot that narrows from the direction of the first end of the housing to the direction of the second end of the housing.

14. The apparatus of claim 13, wherein the housing is vertical, the direction of the first end of the housing is proximate a bottom of the housing, and the direction of the second end of the housing is proximate a top of the housing.

15. The apparatus of claim 14, wherein the air knife is configured to direct the air flow in a horizontal direction.

16. The apparatus of claim 14, wherein the air knife is configured to direct the air flow in a slightly upward or slightly downward direction.

17. The apparatus of claim 13, further comprising an ultraviolet light configured to emit ultraviolet light toward the beverage container while the beverage container is disposed in the wash chamber.

18. The apparatus of claim 17, wherein the ultraviolet light is mounted to the housing of the air knife and the housing of the air knife includes a heat sink formed thereon for discharging heat generated by the ultraviolet light.

19. The apparatus of claim 1, further comprising an ultraviolet light mounted adjacent to the air knife, wherein the ultraviolet light is configured to emit ultraviolet light directed along a radial extending from the axis of rotation, and the air knife is laterally offset from the ultraviolet light and configured to direct air flow along a flow line that is parallel to the radial.

* * * * *